(12) United States Patent
Matsuo

(10) Patent No.: US 7,279,314 B2
(45) Date of Patent: Oct. 9, 2007

(54) CHEMICAL SUBSTANCE HAVING MORPHOGENETIC AND GROWTH-ACCELERATING ACTIVITIES

(75) Inventor: Yoshihide Matsuo, Kamaishi (JP)

(73) Assignee: Marine Biotechnology Institute Co., Ltd. (JP)

(*) Notice: Subject to any disclaimer, the term of this patent is extended or adjusted under 35 U.S.C. 154(b) by 445 days.

(21) Appl. No.: 10/767,260

(22) Filed: Jan. 30, 2004

(65) Prior Publication Data

US 2004/0228854 A1 Nov. 18, 2004

Related U.S. Application Data

(63) Continuation-in-part of application No. PCT/JP03/08840, filed on Jul. 11, 2003.

(30) Foreign Application Priority Data

Jul. 12, 2002 (JP) ............... 2002-203608

(51) Int. Cl.
*C12P 17/18* (2006.01)
*C12P 1/00* (2006.01)

(52) U.S. Cl. .......................... 435/119; 435/41

(58) Field of Classification Search ............... 435/41, 435/119

See application file for complete search history.

(56) References Cited

FOREIGN PATENT DOCUMENTS

JP 2003-189845 8/2003
WO PCT/JP03/08840 1/2004

OTHER PUBLICATIONS

Matsuo et al. Isolation of an Algal Morphogenesis Inducer from a Marine Bacterium. Science. 2005. vol. 307, p. 1598.*
Matsuo, Y., Ishida, R., Matsumoto, T., Tatewaki, M., Suzuki, M. (1997) Yendolipin, a Novel Lipobetaine with an Inhibitory Activity Toward Morphogenesis in Foliaceous Green Alga *Monostroma oxyspernum*, *Tetrahedron* 53:869-876; especially p. 869, second paragraph.
Matsuo, Y., Suzuki, J., Kasai, H., Shizuri, Y., Harayama, S. (2003) Isolation and Phylogenetic Characterization of Bacteria Capable of Inducing Differentiation in the Green Alga *Monostroma oxyspernum* 51:25-35.
Tsujimori, J., Mori, K. (2001) Synthesis of the Racemate of the Stereoisomer at C-6a of BE-40644, a Bioactive Metabolite of *Actinoplanes* sp. with a Sesquiterp;ene-substituted *p*-Benzoquinone Structure, *Biosci. Biotechno. Biochem.* 65:167-171; especially p. 167, scheme 1.
Shizuri, Y., Matsuo, Y. (2002) Natural Products from Marine Bacteria and Marine Organisms; Algal Morphogenesis Induced by Marine Bacteria. *Japanese Society of Phycology* 50:20 (abstract).

* cited by examiner

*Primary Examiner*—Karen Cochrane Carlson
*Assistant Examiner*—Suzanne M. Noakes
(74) *Attorney, Agent, or Firm*—Finnegan, Henderson, Farabow, Garrett, & Dunner, L.L.P.

(57) ABSTRACT

The present invention relates to a method of producing a novel chemical substance capable of inducing morphogenesis, promoting growth of marine foliate green alga that use the microorganisms, and a culturing media for alga containing these novel chemical substances.

9 Claims, 24 Drawing Sheets

50μm gyrB DNA 1143-1191 bp

CHEMICAL SUBSTANCE HAVING MORPHOGENETIC AND GROWTH-ACCELERATING ACTIVITIES

CROSS REFERENCE TO RELATED APPLICATIONS

This application is a continuation-in-part of PCT/JP03/08840 having an international filing date of Jul. 11, 2003, which designated the United States of America. This application also claims priority under 35 U.S.C. § 119 (a) to Japanese Patent application No. 2002-203608 filed on Jul. 12, 2002. The entire contents of all of the above-identified applications are hereby incorporated by reference.

TECHNICAL FIELD

The present invention relates to a novel vitamin effecting substance, derivative, production method, and application thereof.

BACKGROUND ART

Marine green alga such as *Ulva lactuca* and *Monostroma nitidum* are known to form a thallus or become single cells as they become purified when grown in defined synthetic media in indoor culture (L. Provasoli; Ulva. Biol. Bull., 1958, 114, 375. M. Tatewaki, L. Provasoli and I. J. Pintner; J. Phycol., 1983, 19, 409). Moreover, it is also known that when some soil extracts, red alga extracts, brown alga extracts, or certain extracts from marine-derived microorganisms are added to the alga that lost their morphologies in this way, the thallus is formed and the propagation speed increases. (M. Tatewaki, L. Provasoli and I. J. Pintner; J. Phycol., 1983, 19, 409.) However, their active elements and vitamin-like active substances have not been identified, which creates a difficulty in studying their physiology and life or to maintain the culture for a long period using the foliate green alga such as *Ulva lactuca*, and *Monostroma nitidum* under aseptic conditions such as indoor cultivation.

DISCLOSURE OF THE INVENTION

The long-term culturing technique to cultivate the marine foliate green alga using only the defined medium that all components thereof are known allows establishing a practical culturing method to maintain and manage the spore production of cultivating spores, such as edible *Monostroma nitidum* and the like, and to preserve green alga species as well as to study the physiology and lives of target alga. Previously, the inventor of the present invention has found the microorganisms inducing the morphogenetic formation and growth promotion from this point of view (JP-A-2003-189845). However, the active elements and vitamin-like active substances produced by the microorganisms have been poorly understood.

One of the objectives of the present invention is to provide vitamin-like action substances and their derivatives.

In view of the foregoing situations, the inventor of the present invention investigated novel active components in order to isolate the active substances having strong activity from the culture solutions of YM-2-23 strain (Deposited to International Patent Organism Depository, National Institute of Advanced Industrial Science and Technology (Central 6, 1-1-1 Higashi, Tsukuba, Ibaraki, Japan) with deposition number FERM BP-8417 on Aug. 20, 2001 (original depository) (Transfer request accepted to the original depository on Jun. 25, 2003 under the Budapest Treaty)), *Tenacibaculum* sp., YH-1-69 (Deposited to International Patent Organism Depository, National Institute of Advanced Industrial Science and Technology (Central 6, 1-1-1 Higashi, Tsukuba, Ibaraki, Japan) with deposition number FERM BP-8418 on Aug. 20, 2001 (original depository) (Transfer request accepted to the original depository on Jun. 25, 2003 under the Budapest Treaty)), and their analogous strains, to discover if these compounds are novel substances to complete the present invention. Previously, for substances produced by *Flavobacterium, Zobellia*, or *Tenacibaculum* analogous to YM-2-23 strain and/or YM-1-69 strain, the carotenoid derivatives such as lycopene and zeaxanthin are reported, but there have been no cases of isolated chemical substances with foliate alga promoting activity or the morphogenetic control activity, and this will be the first such report in the world.

In other words, the present invention includes the following embodiments.

1. A novel chemical substance 1 having the following physicochemical properties:
   (i) color of substance: colorless;
   (ii) molecular weight: 457;
   (iii) mass spectrometry: FABMS: m/z 456 [M–H]$^-$ (FIG. 1); and
   (iv) nuclear magnetic resonance signal:
   1) $^1$H-NMR(D$_2$O-20 mM Na$_2$HPO$_4$ (pH 9), 750 MHz): (FIG. 2)

δ ppm 0.818 (3H, s), 0.837 (3H, s), 0.882 (3H, s), 0.960 (1H, m), 1.058 (1H, m), 1.167 (1H, m), 1.326 (3H, s), 1.37 (1H, m), 1.38 (1H, m), 1.40 (1H, m), 1.58 (1H, m), 1.61 (2H, m), 1.52 (1H, br d, J=13 Hz), 1.76 (1H, br d, J=14 Hz), 2.024 (1H, m), 2.181 (1H, dd, J=4, 14 Hz), 2.291 (1H, dd, J=14, 16.5 Hz), 7.698 (1H, d, J=7.5 Hz), 7.845 (1H, d, J=7.5 Hz); and 2) $^{13}$C-NMR(D$_2$O-20 mM Na$_2$HPO$_4$ (pH 9), 125 MHz): (FIG. 3)

δ ppm 15.236 (q), 19.037 (t), 20.287 (t), 20.955 (q), 21.835 (q), 25.987 (t), 33.381 (s), 33.636 (q), 37.308 (s), 39.590 (t), 41.199 (t), 42.346 (t), 52.769 (d), 56.381 (d), 79.096 (s), 114.965 (s), 124.399 (d), 139.004 (s), 141.232 (d), 150.282 (s), 152.656 (s), 172.081 (s), 173.538 (s), 174.661 (s).

2. The novel chemical substance 1 according to item 1, which is obtainable from the YM-2-23 strain (FERM BP-8417).

3. The novel chemical substance 1 according to item 1, which is represented by the following formula:

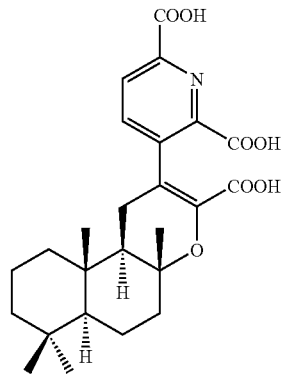

4. The novel chemical substance 1 according to item 1, which has the molecular formula: $C_{25}H_{31}NO_7$.

5. A novel chemical substance 2 having the following physicochemical properties:
   (i) color of substance: colorless; and
   (ii) nuclear magnetic resonance signal:
   $^1$H-NMR(D$_2$O-20 mM Na$_2$HPO$_4$ (pH 9), 500 MHz): (FIG. 4)
   δ ppm 0.815 (3H, s), 0.834 (3H, s), 0.877 (3H, s), 0.949 (1H, m), 1.048 (1H, m), 1.163 (1H, m), 1.297 (3H, s), 1.35-1.40 (3H, m), 1.52-1.63 (4H, m), 1.753 (1H, br d, J=14 Hz), 2.012 (1H, m), 2.158 (1H, m), 2.299 (1H, m), 7.646 (1H, d, J=8.0 Hz), 7.769 (1H, d, J=8.0 Hz).

6. A compound represented by the following formula:

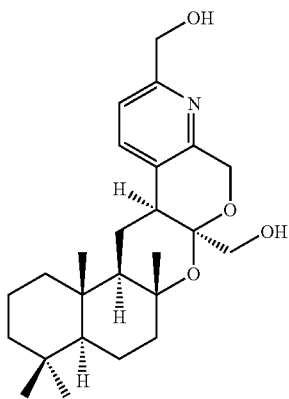

7. A process for producing a novel chemical substance 1, wherein microorganisms capable of producing the novel chemical substance 1 according to any one of items 1-4 are cultured in medium, the novel chemical substance 1 is generated and accumulated in the cultures, and the generated and accumulated novel chemical substance 1 is recovered.

8. A process for producing a novel chemical substance 2, wherein microorganisms capable of producing the novel chemical substance 2 according to item 5 are cultured in medium, the novel chemical substance 2 is generated and accumulated in the cultures, and the generated and accumulated novel chemical substance 2 is recovered.

9. The production process according to item 7, wherein the microorganisms are YM-2-23 strain (FERM BP-8417), or an analogous strain thereof.

10. The production process according to item 8, wherein the microorganisms are YM-2-23 strain (FERM BP-8417), or an analogous strain thereof.

11. Culture medium for algae comprising, as an active ingredient, the novel chemical substance 1 according to any one of items 1-4.

12. Culture medium for algae comprising, as an active ingredient, the novel chemical substance 2 according to item 5.

13. A monomethylated, dimethylated, or trimethylated form of the novel chemical substance 1 obtained by treating the novel chemical substance 1 according to any one of items 1-4 with trimethylsilyldiazomethane.

14. A compound or a derivative thereof obtained by treating the trimethylated form according to item 13 with sodium borohydride.

DETAILED DESCRIPTION OF THE INVENTION

The present invention will be explained in detail hereafter.

The novel chemical substances 1 and 2 of the present invention can be produced using microorganisms. The microorganisms used for the chemical substance production of the present invention are not limited to the microorganisms exhibiting the ability to produce the chemical substance, and these include, for instance, strains that belong to the Cytophaga-Flavobacterium-Bacteriodes complex such as Flavobacterium, Zobellia and Tenacibaculum and the mutant strains derived from these strains. More specifically, they include YM-2-23 strain (FERM BP-8417), Tenacibaculum sp. YM-1-69 (FERM BP-8418), and the mutant strains derived from these strains. Instead of using the YM-1-69 strain and YM-2-23 strain, analogous strains of these strains may be used. The "analogous strains of YM-1-69 strain" include, for instance, strains exhibiting thallus forming activity or growth promoting activity against marine foliate green alga as well as the strains having higher than 85%, or higher than 95%, homology to the nucleotide sequence of the 16S rRNA V3 region gene described by SEQ ID NO:1 or the strain having higher than 72%, or higher than 95% homology to the nucleotide sequence of the gyr B gene described by SEQ ID NO:2. The "analogous strains of YM-2-23 strain" include, for instance, the strains exhibiting the thallus forming activity or growth promoting activity against marine foliate green alga as well as the strains having higher than 65%, or higher than 95%, homology to the nucleotide sequence of the 16S rRNA V3 region gene described by SEQ ID NO:3 or the strain having higher than 72%, higher than 80%, or higher than 95%, homology to the nucleotide sequence of the gyr B gene described by SEQ ID NO:4.

The "YM-1-69 strain analogous strain" and the "YM-2-23 strain analogous strain" includes YM2-10 (MBIC 04671) YM2-11 (MBIC 04672), YM2-12 (MBIC 04673), YM2-13 (MBIC 04674), YM1-66 (MBIC 04663), YM2-24 (MBIC 04684), YM1-51 (MBIC 04662), Zobellia uliginosa (ATCC 14397), YM1-11 (MBIC 04693), T-588 (MBIC 05930), YM2-22 (MBIC 04682), YM2-27 (MBIC 04687), YM2-6 (MBIC 04669), YM1-68 (MBIC 04664), YM1-38 (MBIC 04661), YM2-4 (MBIC 04667), YM2-5 (MBIC 04668), YM2-7 (MBIC 04670), YM2-21 (MBIC 04681 ),YM2-1 (MBIC 04666), T-565 (MBIC 05877), T-424 (MBIC 05876), [Cytophaga] sp. UP7 (MBIC 01484), T-551 (MBIC 05929), Pedobacter heparinus (IFO 12017), T-561 (MBIC 05879), Cyclobacterium marinum (LMG 13164), Cytophaga sp. (MBIC 01539), Cytophaga sp. (MBIC 01599), and Chitinophaga pinensis (DSM 2588).

Among said strains, strains having "MBIC" in their names are available from the Marine Biotechnology Institute Culture Collection (MBIC) (3-75-1 Hirata Kamaishi-city, Iwate, Japan) (seasquirt.mbio.co.jp/mbic/index.php?page=top). Strains having "IFO" in their names are available from the Institute for Fermentation, Osaka (IFO) (17-85 2-Chome Honmachi Juso Yodogawa-ku, Osaka, Osaka, Japan), strains having "ATCC" in their names are available from American Type Culture Collection (ATCC) (12301 Parklawn Drive, Rockville, Md. 20852, U.S.A.), strains having "DSM" in their names are available from Deutsche Sammlung von Mikroorganismen und Zellkulturen GmbH (DSMZ) (Mascheroder Weg 1b, 38124 Braunscheig, Germany), and strains having "LMG" in their name are available from BCCM™/LMG Bateria Collection (Belgian Co-ordinated Collections of Micro-organisms, Laboratorium voor Microbiologie, Universiteit Gent (RUG), K. L. Ledeganckesfaat 35, B-9000 Gent, Brussels, Belgium).

Strains having identical nucleotide sequences of the 16S rRNA V3 region gene and/or the gyr B gene with those of the YM-1-69 strain and the YM-2-23 strain may be selected among the analogous strains.

To culture said organisms, the standard culturing methods for marine bacteria is usually used. For medium, either synthetic medium or natural medium may be used as long as the medium are supplemented with utilizable carbon sources, nitrogen sources, and minerals in balance.

As carbon sources, glucose, starch, dextrin, mannose, fructose, sucrose, lactose, xylose, arabinose, mannitol, and molasses are used alone or in combination. Moreover, hydrocarbons, alcohols, or organic acids may be used depending on the resource utilization capability of the microorganisms.

As nitrogen sources, ammonium chloride, ammonium nitrate, ammonium sulfate, sodium nitrate, urea, peptone, meat extract, yeast extract, dry yeast, corn steep liquor, soy bean flour, and casamino acids are used alone or in combination. In addition, inorganic salts such as sodium chloride, potassium chloride, magnesium sulfate, calcium carbonate, potassium dihydrogen phosphate, magnesium phosphate octahydrate, ferrous sulfate, calcium chloride, manganese sulfate, zinc sulfate, and copper sulfate may be added as needed.

Furthermore, the minor components (for instance, sugars, amino acids and minerals) promoting the bacterial growth may be added ad libitum in the medium or promoting the production of the chemical substance of the present invention.

In order to culture the novel chemical substance 1 or 2 in the bacteria, liquid culture is the most efficient, a temperature of approximately 30° C. is appropriate, and the pH of the medium is normally between 7 to 9, or 7.5 to 8. Sodium hydroxide solution or hydrochloric acid may be used for pH adjustment of the culturing media.

The novel chemical substances 1 and 2 are produced in the media and in the bacterial cells 1 to 4 days after incubating the bacterial cells in the media. One may terminate the cultivation when the substance production in the medium reaches its maximum. More specifically, 3-day incubation may be used.

The novel chemical substance 1 or 2 from the bacterial culture may be isolated in accordance with the manner normally used to isolate and purify microorganism metabolites from the bacterial culture. For example, the culture medium can be separated by filtration or centrifugation to the filtered medium and bacterial cells and then the bacterial cells can be extracted with the solvent such as hydrated methanol and hydrated acetonitrile. Next, the solvent is removed from the extracts under reduced pressure with a rotary evaporator and the like, and the extracts, along with the filtered culture medium, are adsorbed by polystyrene adsorbents (for instance, styrene-divinyl benzene polymer). The adsorbed active substances are washed with water to demineralize and the active substances are eluted with hydrated methanol and hydrated acetonitrile. The eluate is concentrated under reduced pressured with a dry-freezing method to obtain the novel chemical substance 1 or 2 using styrene-divinyl benzene polymers, ion exchange chromatography with negative ion exchange resin, gel filtration chromatography and high performance liquid chromatography. Although the novel chemical substance 2 is a quite unstable substance, the substance slowly changes to the novel chemical substance 1 when the novel chemical substance 2 is stored in a strong alkali solution, such as sodium hydrate or ammonia water. The novel chemical substance 1 is a quite stable chemical substance.

The treatment of the novel chemical substance 1 with appropriate methylating agents (for instance, trimethylsilyldiazomethane) produces the mono-, di-, and tri-methyl forms of the novel chemical substance 1. The molar ratio of trimethylsilyldiazomethane to the novel chemical substance 1 can be adjusted, and appropriate reaction conditions (for instance, reaction temperature, pH setting, or reaction with the presence of diethylaminosulphur trifluoride (DAST)) to selectively obtain mono-, di-, and tri-methyl forms thereof) can be selected.

Furthermore, by treating tri-methyl form with sodium borohydride, Me1H3 with the physiochemical properties described below is obtained. In addition, by changing the polarity of the reaction solvent and reaction speed, a further reduced chemical substance from Me1H3, namely Me1H1, is obtained. Furthermore, by treating Me1H1 with alkyl iodide (for instance, methyl iodide) shown as formula: RI (here R indicates the alkyl group with carbon number 1 to 6 under strong alkali condition, alkyl forms, such as the methylated form Me1H1Me is obtained). These reactions and the information on the product obtained are useful in identifying the novel chemical substances 1 and 2.

Furthermore, by treating Me1H1, obtained by trimethylating the novel chemical substance 1 and treating with sodium borohydride, with hydrochloric acid-methanol for a short period or hydrated methanol for a long period, a cyclized form Me1H1W4 is obtained. Me1H1W4 is easily crystallized in various organic solvents (for instance, acetone, diethyl ether, hexane and dichloromethane chloroform), and its structure can be determined with X-ray crystallographic analysis. Based on the structure of Me1H1W4, the structure of the novel chemical substance 1 can be determined by tracing back the reaction processes of the derivatives.

The novel chemical substances 1 and 2 of the present invention are effective as active elements in the culture medium for alga. The novel chemical substances 1 and 2 can be used by itself or in combination.

Marine foliate green alga is ideal for the alga being cultivated in culture medium for alga. Seaweed in Ulvales, green alga Monostromataceae and Ulvaceae, for instance are included for the marine foliate green alga. More specifically, these green algae include *Monostroma nitidum*, *Monostroma oxyspermum* and *Monostroma angicava* for Monostromataceae, and *Enteromorpha compressa*, *Enteromorpha intestinalis*, *Enteromorpha linza*, *Ulva conglobata*, and *Ulva perusa* for Ulvaceae.

For the medium used for cultivating the marine foliate green alga, a medium similar to the medium used with conventional methods (culturing method to result in unicellular marine foliate green alga) may be used except that active components, namely the novel chemical substance 1 and/or 2 are supplemented. For instance, ASP7 medium, PES medium and/or PESI medium, or simply sterilized sea water may be used. The effective concentrations of the novel substance 1 and/or 2 in the medium are not limited specifically as long as they are in the concentration range to induce the thallus formation, but may be in the range of $10^{-12}$ to $10^{-3}$ μg/ml.

There is no temperature limitation in growing the marine foliate green alga as long as they can survive and it is appropriate that the temperature is in the range of 15 to 25° C.

EXAMPLES

Figure 1:
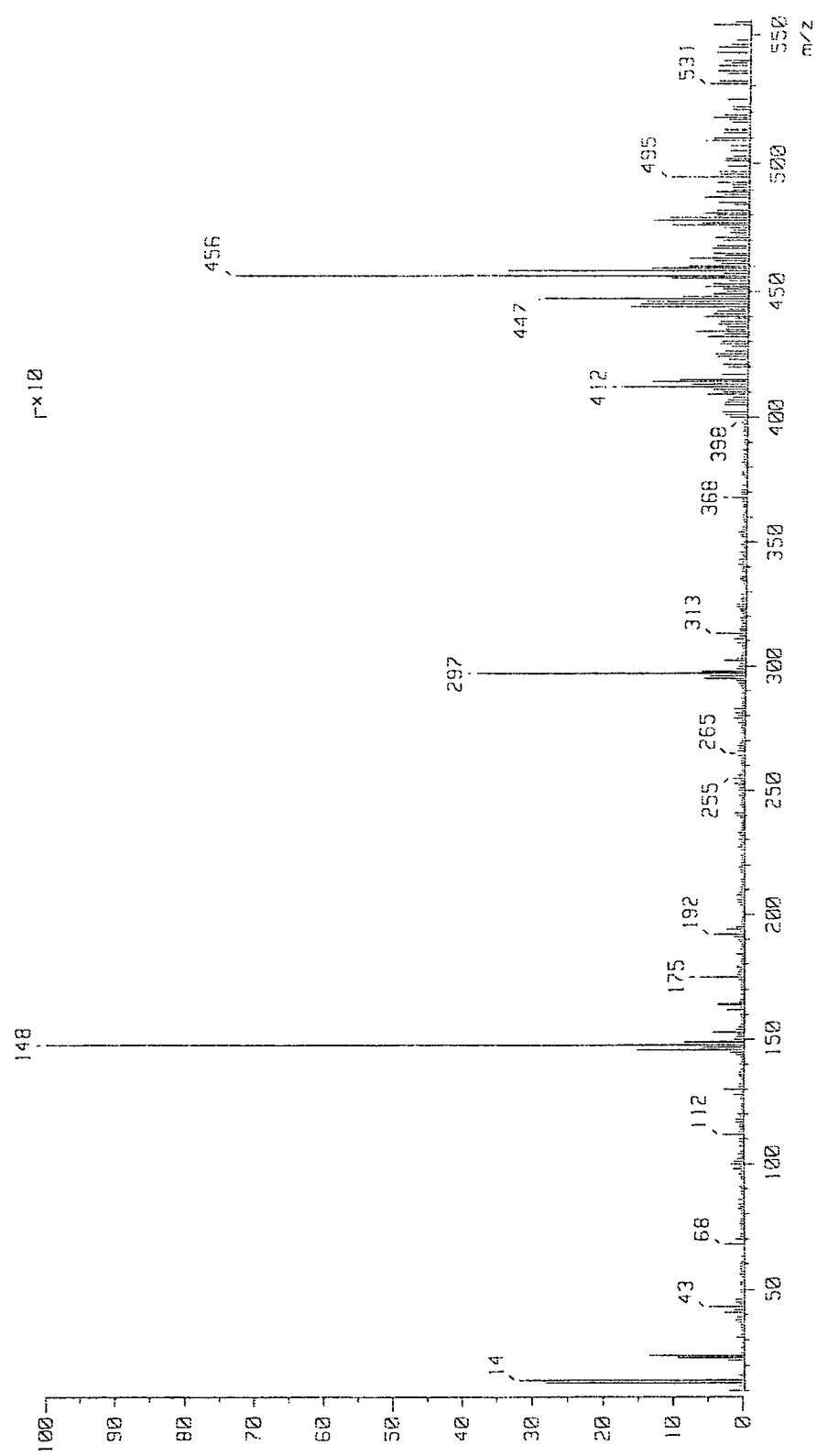
FIG. 1 shows a mass spectrum of the novel chemical substance 1.

The present invention is explained hereafter, with reference to the examples. However, the present invention does not limit its technical scopes to these examples.

Referential Example 1

Isolation of the Microorganisms

The strains used for the present invention were isolated by the procedures described below. Approximately 1 gram of freshly collected alga was added in 10 ml of sterile sea water and then vortexed vigorously for approximately 1 minute. The supernatant was serially diluted further with sterile sea water to 1/10 and 1/100, and 100 µl was inoculated onto 1/10 marine agar plates and then spread to the entire plate with a sterilized Conradi stick. After culturing for 2-3 days at room temperature, grown yellow-red colonies were individually inoculated in marine agar plates and kept in culture until a single colony was isolated. These cells were transferred into the wells of either 24- or 48-well microtitre plates containing 2 or 1 ml, respectively, of an ASP7 medium, and then approximately 20 cells of single celled *Monostroma oxyspermum* were added. Each single colony from the isolated strains was directly inoculated to two wells using a sterile inoculation loop. The microtitre plates were incubated at 19-22° C. with a 14 h/10 h light/dark cycle for 5 days, and the thallus formation of *Monostroma oxyspermum* was confirmed under an inverted microscope. Strains exhibiting the thallus formation were confirmed by re-examination in a similar manner to that described above. After these screening steps described above, the YM-1-69 strain and YM-2-23 strain were isolated as the strains exhibiting the thallus forming activity. The YM-1-69 strain was isolated from *Halimeda opuntia* (Codiales, Chlorophyta) and the YM-2-23 strain was isolated from *Monostroma nitidum* (Ulvales, Chlorophyta).

Referential Example 2

Identification of the Microorganisms

The DNA sequences of the 16S rRNA V3 regions and gyr B genes of the microorganisms obtained in Referential Example 1 were determined. The DNA sequences of the 16S rRNA V3 regions and gyr B gene of YM-1-69 strain are shown in Sequence 1 and Sequence 2, respectively. In addition, the DNA sequences of the 16S rRNA V3 regions and gyr B gene of YM-2-23 strain are shown in Sequence 3 and Sequence 4, respectively. The obtained DNA sequences were analyzed using the searching database (DDBJ-fasta) and the sequences were shown to have high homology to the microorganisms shown in Table 1.

TABLE 1

| Sequence | Homology (%) | Organisms with Related Sequences | Accession Number |
|---|---|---|---|
| SEQ ID NO:1 | 95.26 | *Tenacibaculum amylolyticum* | AB032505 |
| SEQ ID NO:2 | 94.18 | *Zobellia uliginosa* | M62799 |
| SEQ ID NO:3 | 84.91 | *Tenacibaculum amylolyticum* | AB032586 |
| SEQ ID NO:4 | 78.18 | *Zobellia uliginosa* | AB034224 |

TABLE 2

| Physiochemical Properties | YM-1-69 | YM-2-23 |
|---|---|---|
| Gram Staining | − | − |
| Catalase Activity | + | + |
| Oxidase Activity | + | + |
| OF Test | o | F |
| Mg or Ca Requirements | + | + |
| Nitrate Reduction | + | + |
| Indole Production | − | − |
| Gelatin Hydrolysis | − | − |
| Starch Hydrolysis | + | + |
| DNA Hydrolysis | + | + |
| Tween80 Hydrolysis | + | + |
| Esculin Hydrolysis | + | + |
| Arginine Dihydrolase Activity | − | − |
| Urease Activity | − | − |
| β-galactosidase activity | − | + |
| Utilization of Citric Acid Simons Medium | − | − |
| Christensen Medium | − | − |

+: Positive,
−: Negative

Based on the results of Table 1 and Table 2, YM-1-69 strain was identified as *Tenacibaculum* sp. and YM-2-23 strain was identified as *Flavobacterium* sp.

Example 1

Monostroma Oxyspermum Culture

*Monostroma oxyspermum* sterilized with experimental antibiotics lose their leafy morphology as seen in natural environment in synthetic medium such as ASP7, and most of them become unicellular.

One ml of modified ASP7 medium was added in the wells of the first row of 48-well microtitre plates (Iwaki, hereafter abbreviated as 48-MTP) and 0.9 ml of modified ASP7 medium was added in the wells of the second and subsequent rows. Eleven µl of the active substance fraction of the target was added individually and mixed well by pipetting in the wells on the first row, followed by adding 100 µl of this mixed solution to the wells on the next row. By repeating this procedures subsequently for 8 to 18 times for each fraction, a ten-fold serial dilution can be prepared in 8 to 18 steps. 100 µl that remained in solution in the wells on the last row was discarded. Here, 100 µl of *Monostroma oxyspermum* culture medium was diluted subsequently so that the final cell concentration of 10 to 20 cells per 1 ml, was delivered to all wells of 48-MTP to bring the total amount of solution to 1 ml. This 48-MTP was incubated under a continuous light period at 22° C. for 3 to 5 days, and then the formation of a thallus was examined under an inverted microscope. The lowest concentration of the sample exhibiting thallus-forming activity was determined as the minimum effective concentration (MEC), and the sample with the lowest MEC is considered to contain the most active substances. The MEC is used as an index for isolation.

Figure 5:
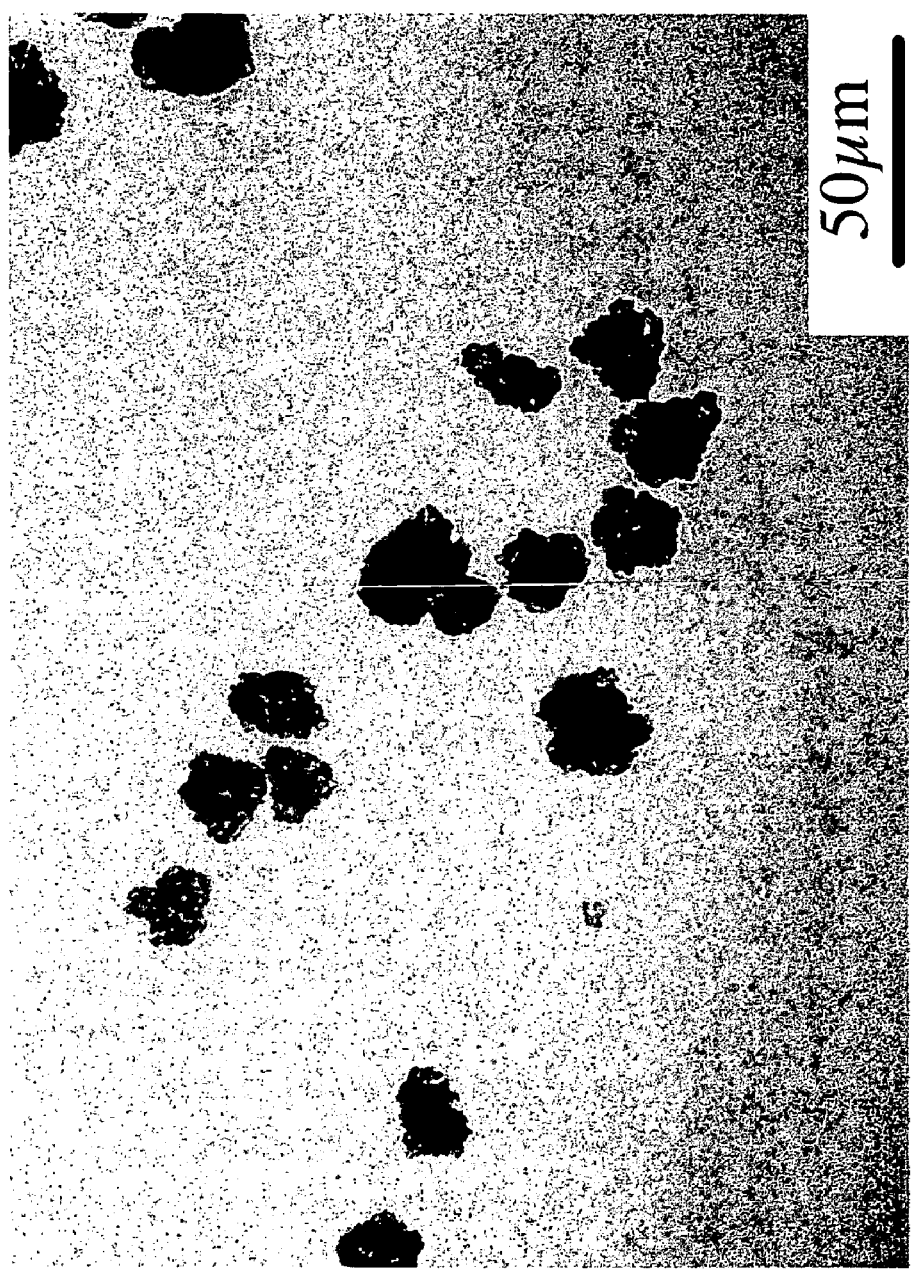
FIG. 5 is a picture of *Monostroma oxyspermum* media cultured for 5 days without the samples in the *Monostroma oxyspermum* culturing experiment of Example 1.
Figure 6:
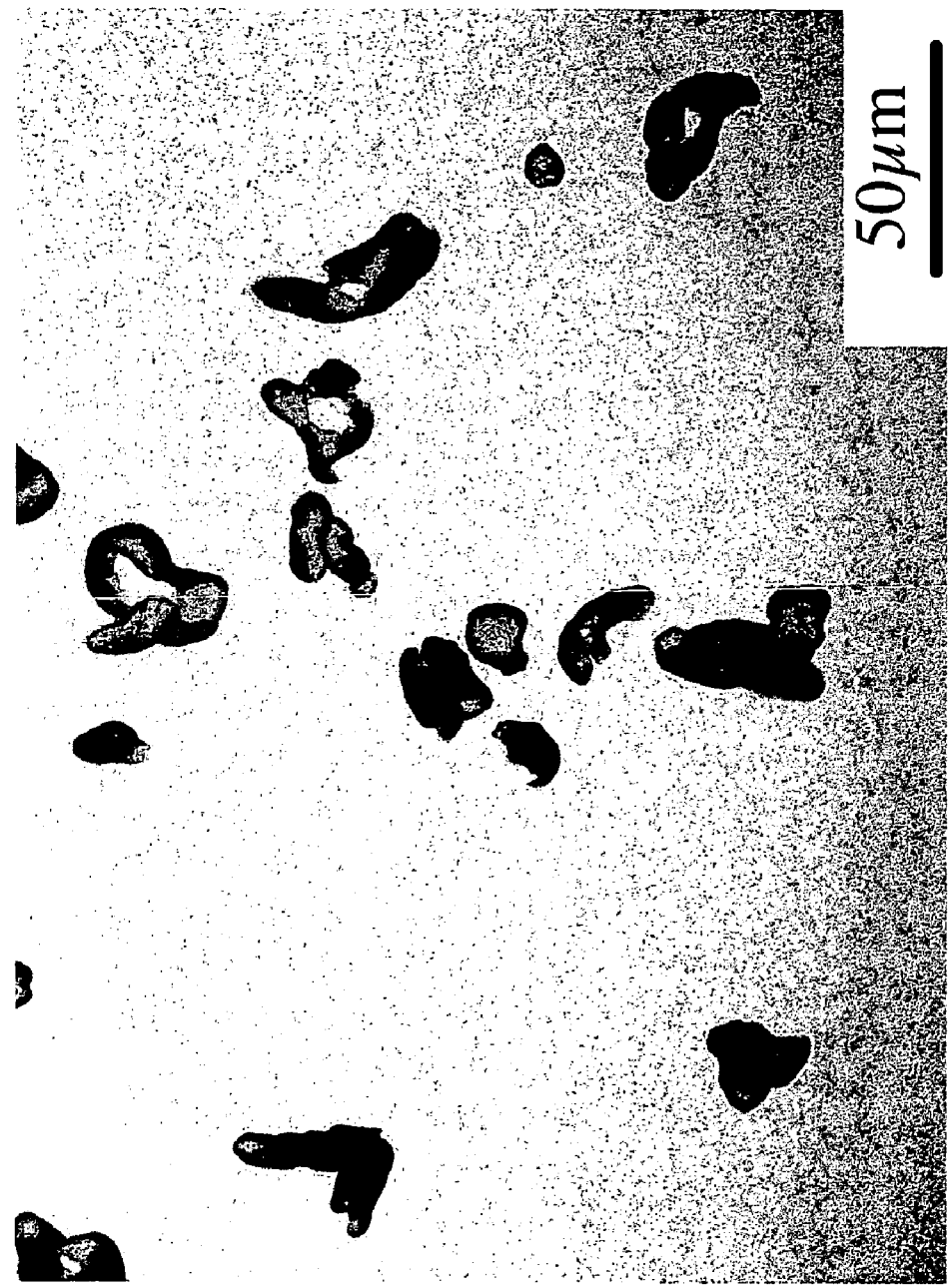
FIG. 6 is a picture of *Monostroma oxyspermum* media cultured for 5 days with the samples in the *Monostroma oxyspermum* culturing experiment of Example 1.

FIG. 5 shows a picture of *Monostroma oxyspermum* media cultured for 5 days without the samples in the culturing experiment. In addition, FIG. 6 shows a picture of *Monostroma oxyspermum* media culture for 5 days with the samples. When the active substances were present, the formation of thallus was observed as shown in FIG. 6.

TABLE 3

| Modified ASP7 Medium (1 L, pH 7.8-8.0) | |
| --- | --- |
| Distilled Water | 950 ml |
| NaCl | 25 g |
| $MgSO_4 \cdot 7H_2O$ | 9 g |
| KCl | 700 mg |
| $CaCl_2$ | 840 mg |
| Tris HCl | 1 g |
| $NaNO_3$ | 50 mg |
| $Na_2$-glyceroPO$_4$ | 20 mg |
| $Na_2SiO_3 \cdot 9H_2O$ | 70 mg |
| Vitamin B12 | 1 µg |
| Nitrilotriacetic Acid | 70 mg |
| Vitamin Mix S3 *1 | 10 ml |
| PII metals *2 | 30 ml |
| S2 metals *3 | 5 ml |

TABLE 4

| *1 Vitamin Mix S3 | |
| --- | --- |
| Distilled Water | 100 ml |
| Thiamin Hydrochloride | 5 mg |
| Nicotinic Acid | 1 mg |
| Calcium Pantothenate | 1 mg |
| p-Aminobenzoic Acid | 0.1 mg |
| Biotin | 0.01 mg |
| Inositol | 50 mg |
| Thymine | 30 mg |
| Folic Add | 0.02 mg |

TABLE 5

| *2 PII metals | |
| --- | --- |
| Distilled Water | 1000 ml |
| $Na_2$-EDTA | 1 g |
| $FeCl_3 \cdot 6H_2O$ | 48 mg |
| $H_3BO_3$ | 1.13 g |
| $MnCl_3 4H_2O$ | 144 mg |
| $ZnCl_2$ | 5.2 mg |
| $CoCl_2 \cdot 6H_2O$ | 4 mg |

TABLE 6

| *3 S2 metals | |
| --- | --- |
| Distilled Water | 500 ml |
| $Na_2MoO_4 \cdot 2H_2O$ | 63 mg |
| NaBr | 640 g |
| $SrCl_2 \cdot 6H_2O$ | 304 mg |
| RbCl | 14 mg |
| LiCl | 61 mg |
| KI | 0.65 mg |
| $V_2O_5$ | 0.18 mg |

Example 2

Isolation and Purification of the Novel Chemical Substance 1

YM-2-23 strain (FERM BP-8417) was used as a seed bacterium. For main culture medium, marine broth (Difco, 37.4 g/l, or prepared by mixing each reagent in accordance with the displayed components). The corresponding strain was cultivated in 50 ml of marine broth in a 100 ml conical flask on a reciprocal shaker (100 rpm) at 30° C. for 24 hours, and then the entire medium was transferred in a 1 liter conical flask with a baffle containing 450 ml of the medium to incubate for another 24 hours under the same condition. The main culture was carried out in 800 of the medium in 16 units of a 1 liter conical flask with a baffle containing 800 ml of the medium each on a reciprocal shaker (130 rpm) and then further incubated in a 10 units of 1 liter conical flask containing 450 ml of the medium on a reciprocal shaker (100 rpm) at 30° C. for 3 days. A total of approximately 18 liters of the culture media obtained in this way was centrifuged. The bacteria cells were stored in a −20° C. freezer and the filtered culture media was stored at 4° C. The bacteria cells of 4 batches of said main culture (approximately 72 liters) were extracted twice with 1200 ml of 50% acetonitrile solution, and then concentrated. The concentrated solution and approximately 72 liters of the filtered culture media were mixed and then adsorbed by 2500 ml of the stryrene-divinyl benzene polymer Diaion HP-20 (Mitsubishi Chemicals). The resin was washed with 6000 ml of 10% acetonitrile solution to demineralize, and then eluted with 6000 ml of 50% acetonitrile solution to obtain a thallus formation inducing fraction. The eluted fraction was adsorbed by Toyo-Pearl DEAE-650(M) (Tosoh), and then washed with 180 mM NaCl-20% acetonitrile, followed by elution with 450 mM NaCl-20% acetonitrile to obtain the active fraction. After concentrating the eluted fraction under reduced pressure to eliminate acetonitrile, the fraction was adsorbed with 500 ml of Diaion HP-20 (Mitsubishi Chemicals) and washed with 1000 ml of 10% acetonitrile solution to demineralize, to obtain the active fraction with 1000 ml of 50% acetonitrile solution. After concentration under reduced pressure, the active fraction was freeze-dried to obtain a thallus formation inducing fraction. The culture and two batches of crude fraction (culture medium approximately 140 liters) were mixed and purified by gel filtration chromatography (Amersham Biosciences, Sephacryl S-100 HR 25 mm (inner diameter)×1200 mm (length)) using 100 mM NaCl-20 mM $Na_2HPO_4$-20% acetonitrile solution (pH 9) as a mobile phase to obtain the fraction with thallus inducing activity. This active fraction was concentrated, demineralized, freeze-dried, and isolated with high performance liquid chromatography (Amersham Biosciences, RESOURCE RPC3ML, 6.4 mm (inner diameter)×100 mm (length)×2 in series) using 14 to 22% acetonitrile-5 g $(NH_4)2CO_3$/l solution as a mobile phase. Then, the active fraction was freeze-dried, and further purified with high performance liquid chromatography (Amersham Biosciences, RESOURCE RPC3ML, 6.4 mm (inner diameter)×100 mm (length)×2 in series) using 5-25% acetonitrile–1% $NH_3$ as a mobile phase to finally obtain approximately 140 μg of the novel chemical substance 1 with said physiochemical properties of the present invention.

Example 3

Isolation and Purification of the Novel Chemical Substance 2

Figure 4:
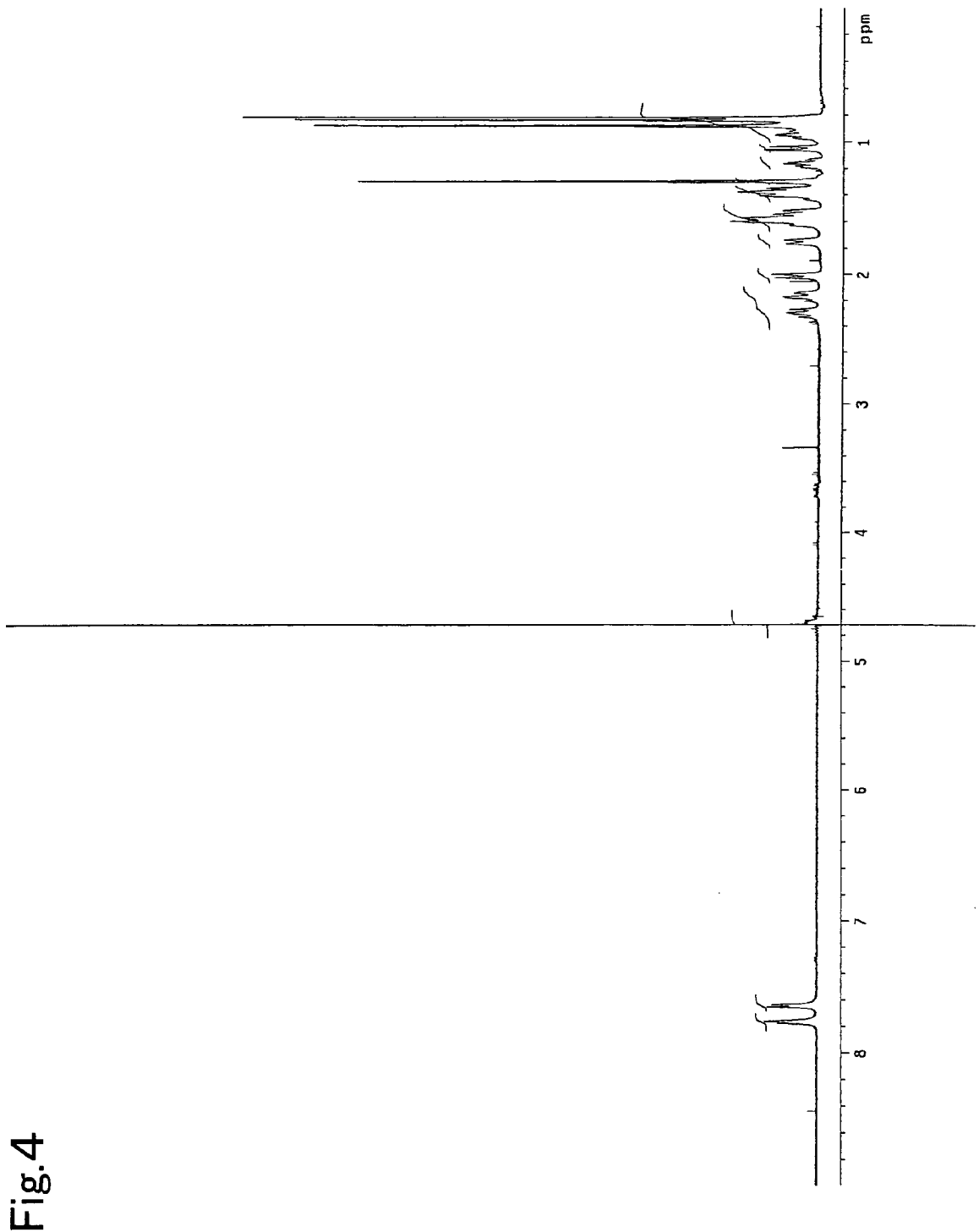
FIG. 4 shows a $^1$H-NMR spectrum of the novel chemical substance 2.

It is known that the novel chemical substance 1 isolated in accordance with Example is a changed form of the novel chemical substance under the strong alkali conditions of 5 to 25% acetonitrile-1% $NH_3$ in the final purification process. In addition, the novel chemical substance 1 co-presents with the novel chemical substance 2 in the pre-purified culture supernatant. The novel chemical substance 2 is quite unstable in neutral to weak acidic conditions, whereas the novel chemical substance 1 induced under alkali condition is relatively stable. FIG. 4 shows a $^1$H-NMR spectrum of the novel chemical substance 2 isolated with the high performance liquid chromatography (Amersham Biosciences, RESOURCE RPC3ML, 6.4 mm (inner diameter)×100 mm (length)×2 in series) using 17% acetonitrile-5 g $(NH_4)2CO_3$+5 ml $NH_3$/l solution as a mobile phase in the final process of the purification.

Example 4

Preparation of a Methylated Form of a Novel Chemical Substance 1 and a Derivative Thereof and their Physicochemical Properties A novel chemical substance 1 (about 140 μg) was dissolved in 40 μl of methanol, 160 μl of benzene and 100 μl of trimethylsilyldiazomethane (10%, n-hexane solution, manufactured by Tokyo Kasei Kogyo Co., Ltd.) were added thereto, the mixture was thoroughly stirred, and the resultant was allowed to react at room temperature for 2 hours. Small portions of acetic acid were gradually added until the yellow color of diazomethane disappeared, a solvent was removed by distillation using an evaporator, followed by separation by high-performance liquid chromatography (TSKgel ODS-80Ts, 4.6 mm (inner diameter)×150 mm (length), Tosoh) using 50% to 100% acetonitrile-water as a mobile phase. As a result, a trimethylated form of a novel chemical substance 1 (hereafter abbreviated as "Me1") was substantially quantitatively obtained (yield: about 152 μg, 99%). This trimethylated form provides for Me1B through gradual substitution of one methoxy (—$OCH_3$) with deuterium methoxy (—$OCD_3$) in deuterium methanol, which is a solvent for NMR spectrometry. Me1 (about 152 μg) was dissolved in 200 μl of methanol, 1 mg of sodium borohydride was added under ice cooling, and the resultant was subjected to reduction for 1 hour. The reaction solution was separated by high performance liquid chromatography (TSKgel ODS-80Ts, 4.6 mm (inner diameter)×150 mm (length), Tosoh) using 50% to 100% acetonitrile-water as a mobile phase. As a result, a reduced form of Me1 (hereafter abbreviated as "Me1H3") was obtained at high yield (yield: about 140 μg, 98%). The total amount of Me1H3 obtained above was dissolved in 400 μl of dried diethyl ether, 100 μl of solution of sodium borohydride in ethanol (20 mg/ml) was added thereto at room temperature, and the resultant was allowed to react at room temperature for 150 minutes. An aqueous solution of saturated sodium chloride (100 μl) was added thereto, the resultant was stirred for 10 minutes, and a solvent was removed by distillation using an evaporator. A reaction solution was separated by high performance liquid chromatography using 50% to 100% acetonitrile-water as a mobile phase (TSKgel ODS-80Ts, 4.6 mm (inner diameter)×150 mm (length), Tosoh). As a result, a highly reduced form of Me1 (hereafter abbreviated as "Me1H1") was substantially quantitatively obtained (yield: about 123 μg, 99%). Further, the total amount of Me1H1 obtained above was dissolved in 400 μl of dried dimethyl sulfoxide, 1 mg of finely pulverized sodium hydroxide was added thereto, 40 μl of methyl iodide was added thereto, and the resultant was then allowed to react at room temperature for 30 minutes. Distilled water (500 μl) was added under ice cooling to terminate the reaction. Thereafter, the reaction solution as such was separated by high performance liquid chromatography using 50% to 100% acetonitrile-water as a mobile phase (TSKgel ODS-80Ts, 4.6 mm (inner diameter)×150 mm (length), Tosoh). As a result, a methylated form of Me1H1 (hereafter abbreviated as "Me1H1Me") was substantially quantitatively obtained (yield: about 135 μg, 99%).

The obtained compounds had physiochemical properties as shown below.

Figure 7:
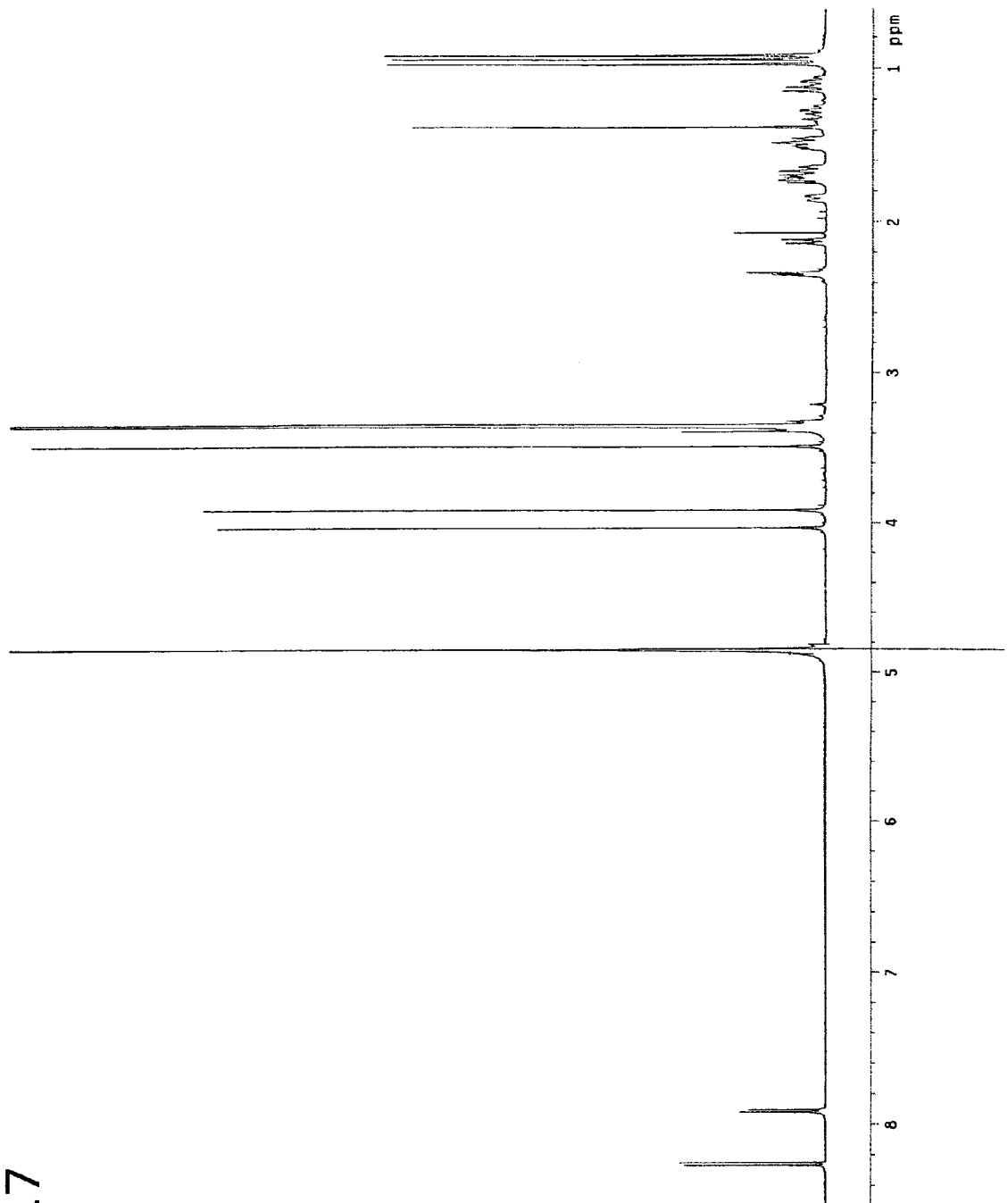
FIG. 7 shows a $^1$H-NMR spectrum of Me1.

[Physicochemical Properties of Me1]
1. Color of substance: colorless
2. Molecular weight: 499
3. Mass spectrometry: FABMS: m/z 500 [M+H]+
4. Nuclear magnetic resonance signal:
1) $^1$H-NMR (deuterium methanol, 500 MHz): (FIG. 7)
δ ppm 0.916 (3H, s), 0.941 (3H, s), 0.973 (3H, s), 1.086 (1H, ddd, J=3.5, 12.5, 13.0 Hz), 1.136 (1H, dd, J=2.0, 12.0 Hz), 1.271 (1H, ddd, J=4.0, 13.0, 14.0 Hz), 1.380 (3H, s), 1.47 (2H, m), 1.50 (1H, m), 1.65 (1H, m), 1.69 (2H, m), 1.73 (1H, m), 1.84 (1H, m), 2.130 (1H, ddd, J=3.5, 7.0, 12.5 Hz), 2.34 (2H, m), 3.488 (3H, s), 3.914 (3H, s), 4.034 (3H, s), 7.911 (1H, d, J=8.0 Hz), 8.258 (1H, d, J=8.0 Hz)

Figure 8:
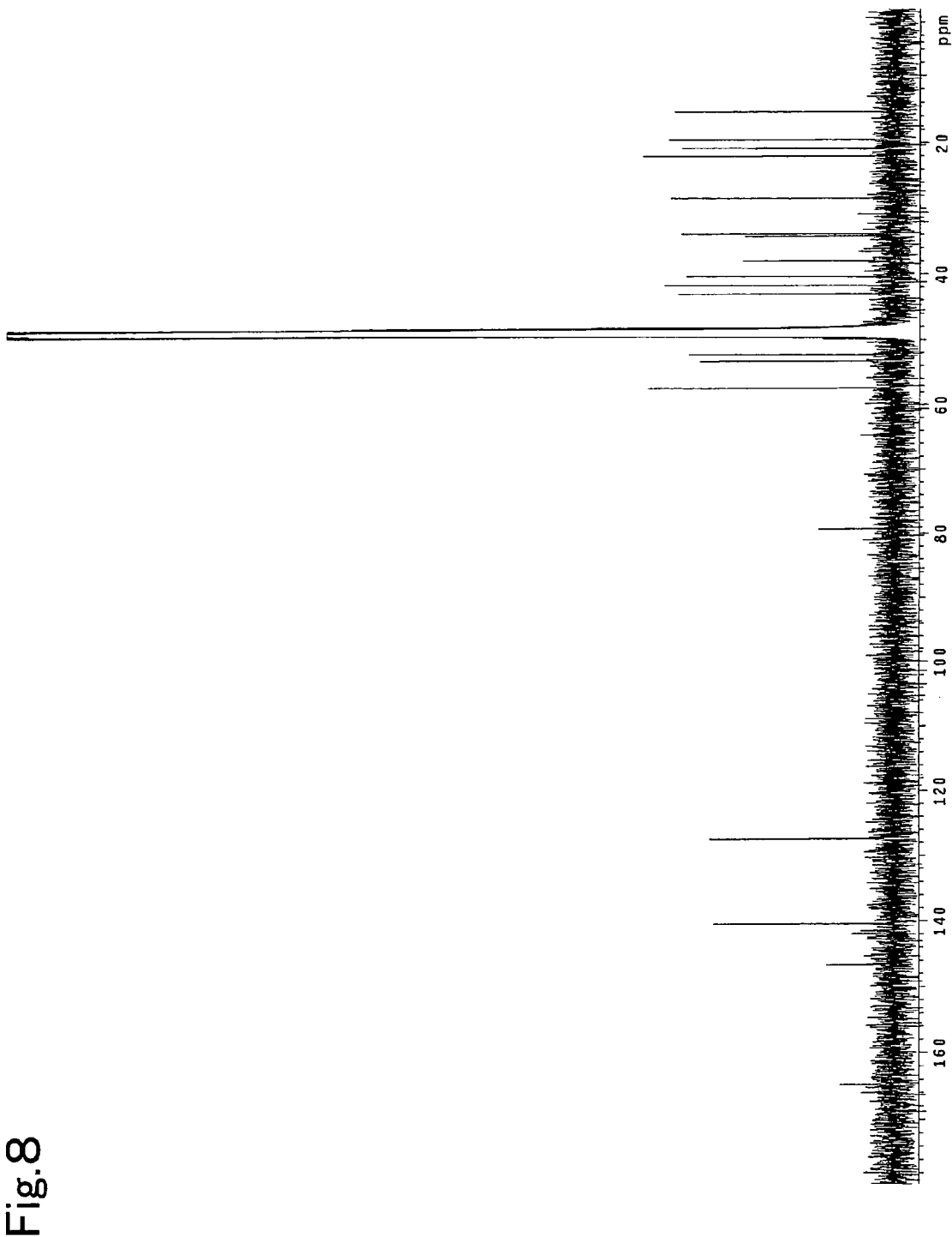
FIG. 8 shows a $^{13}$C-NMR spectrum of Me1.

2) $^{13}$C-NMR (deuterium methanol, 125 MHz): (FIG. 8)
δ ppm 15.413 (q), 19.559 (t), 20.797 (t), 20.961 (q), 21.981 (q), 28.416 (t), 33.855(q), 34.164 (s), 37.928 (s), 40.356 (t), 41.722 (t), 42.996 (t), 52.266 (q), 53.255 (q), 52.255 (q), 53.328 (q), 57.432 (d), 79.291 (s), 120.0 (s), 127.392 (d), 140.407 (d), 141.6 (s), 146.659 (s), 149.8 (s), 164.761 (s), 166.027 (s), 167.402 (s)

5. Solubility: hardly soluble in water and DMSO, soluble in hydrated solvent such as an aqueous solution of 50% to 100% methanol or an aqueous solution of 50% to 100% acetonitrile, and hardly soluble in less-polar organic solvents such as hexane or chloroform.

Figure 9:
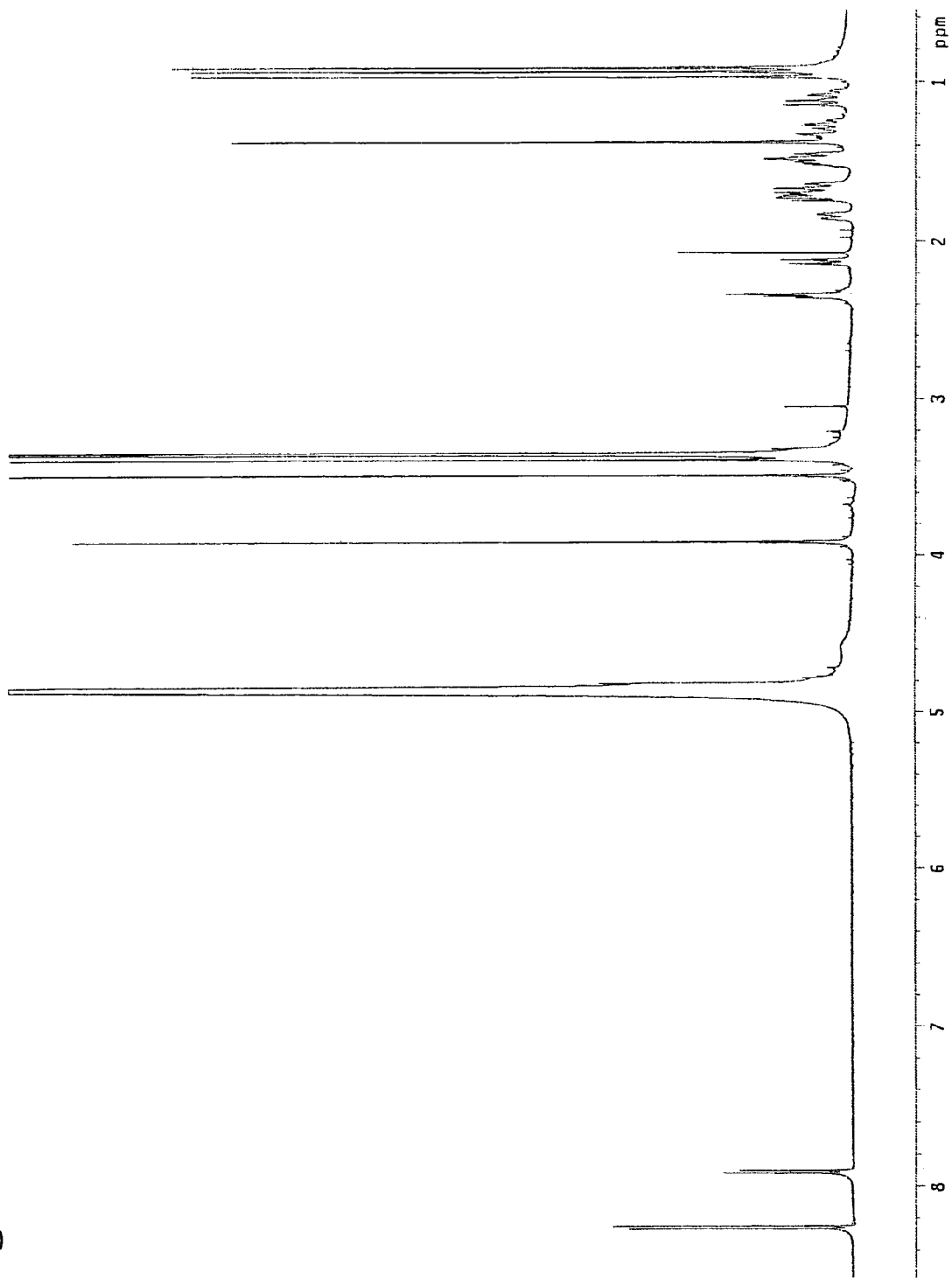
FIG. 9 shows a $^1$H-NMR spectrum of Me1B.

[Physicochemical Properties of Me1B]
1. Color of substance: colorless
2. Molecular weight: 502
3. Mass spectrometry: FABMS: m/z 503 [M+H]$^+$
4. Nuclear magnetic resonance signal:
$^1$H-NMR (deuterium methanol, 500 MHz): (FIG. 9)
δ ppm 0.916 (3H, s), 0.941 (3H, s), 0.973 (3H, s), 1.086 (1H, ddd, J=3.5, 12.5, 13.0 Hz), 1.136 (1H, dd, J=2.0, 12.0 Hz), 1.271 (1H, ddd, J=4.0, 13.0, 14.0 Hz), 1.380 (3H, s), 1.47 (2H, m), 1.50 (1H, m), 1.65 (1H, m), 1.69 (2H, m), 1.73 (1H, m), 1.84 (1H, m), 2.130 (1H, ddd, J=3.5, 7.0, 12.5 Hz), 2.34 (2H, m), 3.488 (3H, s), 3.914 (3H, s), 7.911 (1H, d, J=8.0 Hz), 8.258 (1H, d, J=8.0 Hz)
5. Solubility: hardly soluble in water and DMSO, soluble in hydrated solvent such as an aqueous solution of 50% to 100% methanol or an aqueous solution of 50% to 100% acetonitrile, and hardly soluble in less-polar organic solvents such as hexane or chloroform.

Figure 10:
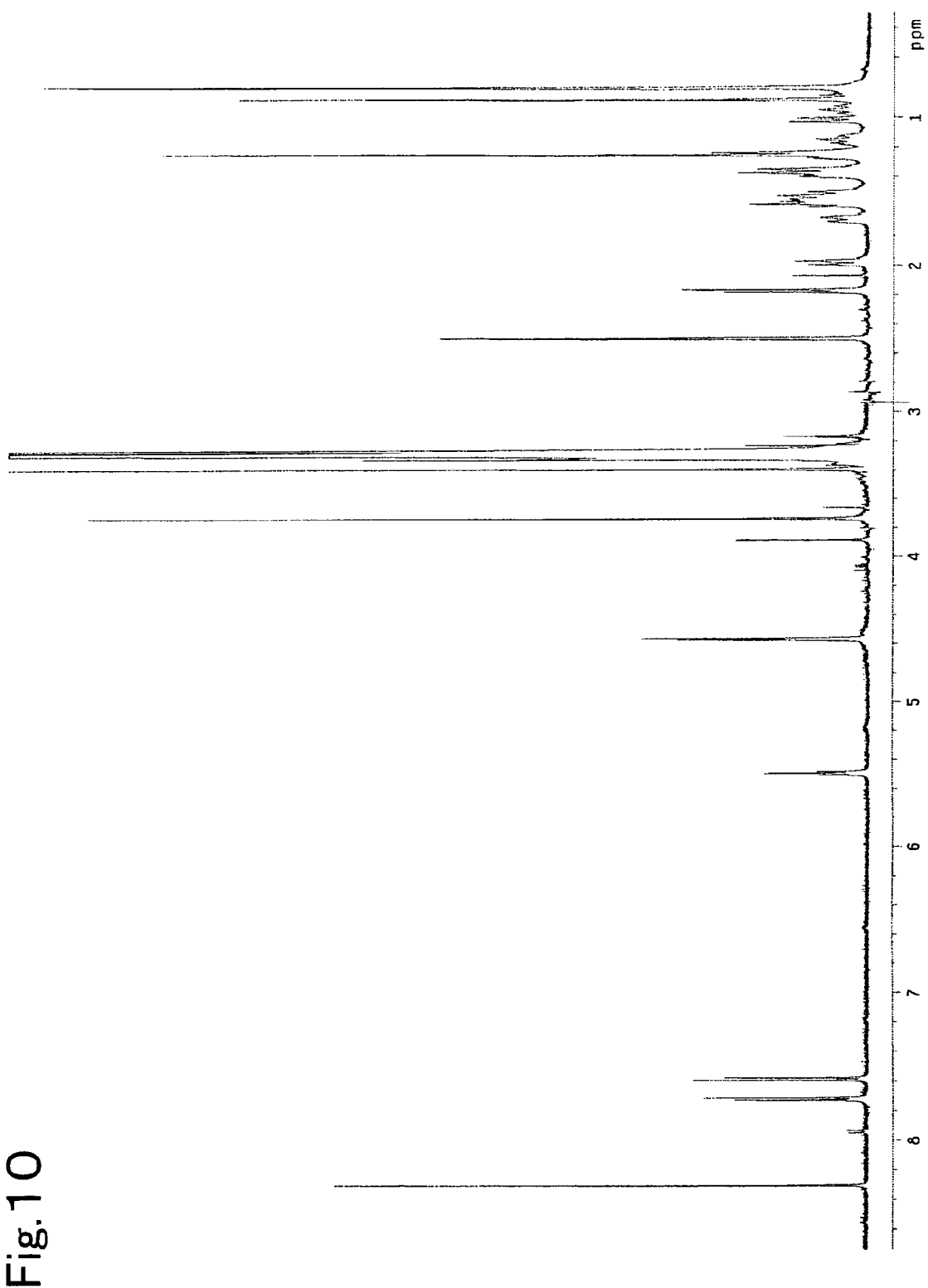
FIG. 10 shows a $^1$H-NMR spectrum of Me1H3.

[Physicochemical Properties of Me1H3]
1. Color of substance: colorless
2. Molecular weight: 471
3. Mass spectrometry: FABMS: m/z 472 [M+H]$^+$
4. Nuclear magnetic resonance signal:
1) $^1$H-NMR (DMSO-d6, 500 MHz): (FIG. 10)
δ ppm 0.802 (3H, s), 0.810 (3H, s), 0.885 (3H, s), 0.951 (1H, m), 1.018 (1H, m), 1.150 (1H, m), 1.254 (3H, s), 1.35 (1H, m), 1.36 (1H, m) 1.37 (1H, m), 1.50 (1H, m), 1.54 (1H, m), 1.57 (1H, m), 1.58 (1H, m), 1.688 (1H, m), 1.984 (1H, m), 2.174 (2H, br d, J=8.5 Hz), 3.399 (3H, s), 3.741 (3H, s), 4.570 (2H, br d, J=5.5 Hz), 5.495 (1H, br t, J=5.5 Hz), 7.587 (1H, d, J=8.0 Hz), 7.722 (1H, d, J=8.0 Hz)
2) $^{13}$C-NMR (deuterium methanol, determination of chemical shift based on HMBC (Heteronuclear Multiple Bond Coherence) and HSQC (Heteronuclear Single Quantum Coherence) spectrum):
δ ppm 14.2(q), 17.7(t), 19.0(t), 20.0(q), 21.1(q), 26.7(t), 33.0 (q), 33.3 (s), 36.1 (s), 38.3 (t), 40.1 (t), 41.1 (t), 51.2 (q), 51.2 (d), 52.0 (q), 55.2 (d), 63.7 (t), 76.8 (s), 119.2 (s), 121.8 (d), 134.1 (s), 138.3 (d), 146.2 (s), 159.8 (s), 162.8 (s), 166.2 (s)
5. Solubility: hardly soluble in water and 100% methanol, soluble in hydrated solvent such as an aqueous solution of 50% methanol or an aqueous solution of 50% acetonitrile, soluble in DMSO, and hardly soluble in less-polar organic solvents such as hexane or chloroform.

Figure 11:
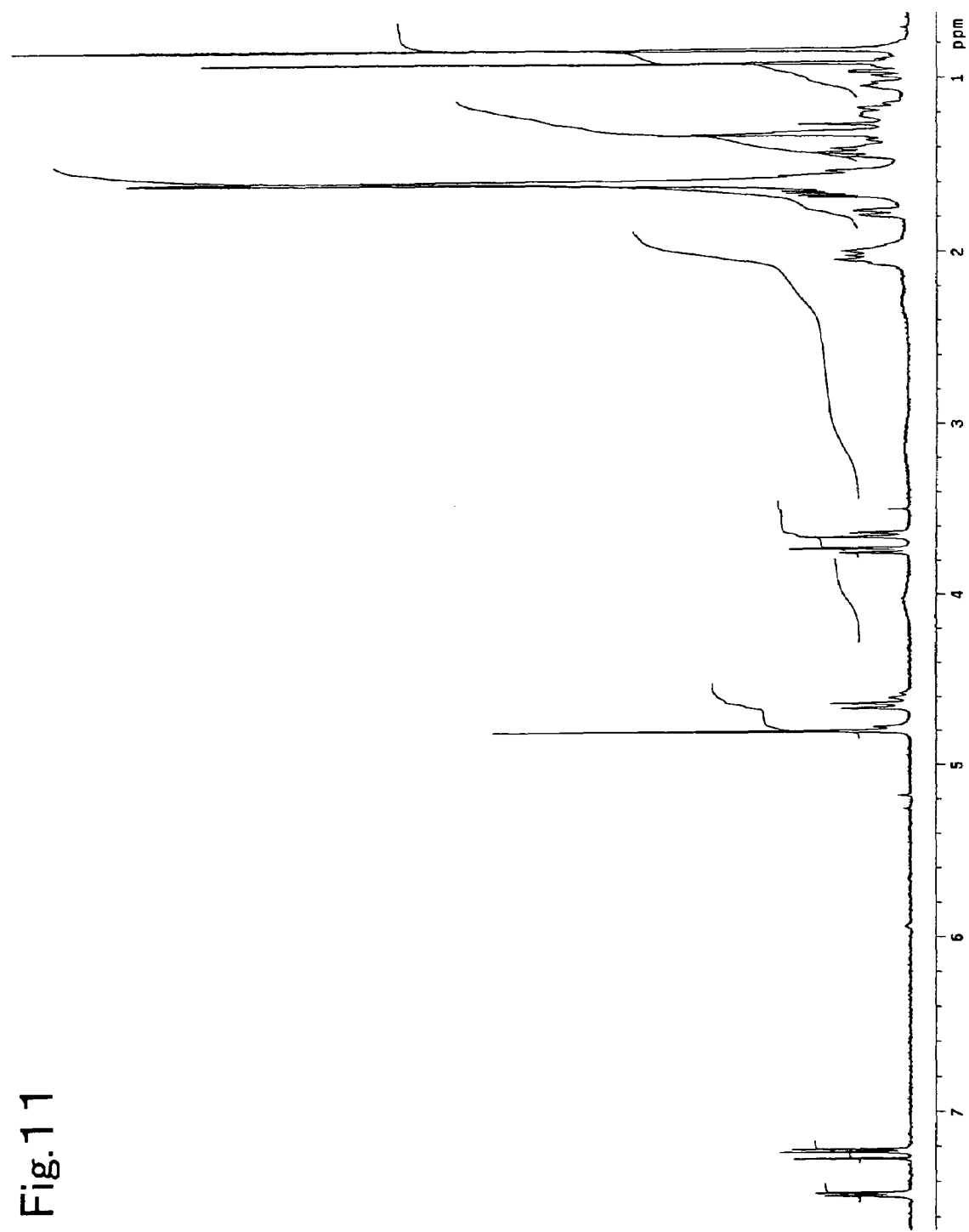
FIG. 11 shows a $^1$H-NMR spectrum of Me1H1.

[Physicochemical Properties of Me1H1]
1. Color of substance: colorless
2. Molecular weight: 415
3. Mass spectrometry: FABMS: m/z 416 [M+H]$^+$
4. Nuclear magnetic resonance signal:
1) $^1$H-NMR (deuterium chloroform, 500 MHz): (FIG. 11)
δ ppm 0.842 (6H, s), 0.918 (3H, s), 0.97 (1H, m), 1.04 (1H, m), 1.18 (1H, m), 1.327 (3H, s), 1.36 (1H, m), 1.42 (1H, m), 1.45 (1H, m), 1.55 (1H, m), 1.58 (1H, m), 1.64 (1H, m), 1.667 (1H, dd, J=5.5, 12 Hz), 1.78 (1H, m), 2.02 (2H, m), 2.05 (1H, m), 3.650 (2H, d, J=12 Hz), 4.647 (2H, d, J=14 Hz), 4.801 (2H, br s), 7.226 (1H, d, J=8.0 Hz), 7.474 (1H, d, J=8.0 Hz)
2) $^{13}$C-NMR (deuterium chloroform, determination of chemical shift based on HMBC (Heteronuclear Multiple Bond Coherence) and HSQC (Heteronuclear Single Quantum Coherence) spectrum)
δ ppm 15.1 (q), 18.4 (t), 19.8 (t), 20.9 (q), 21.5 (q), 25.1 (t), 33.2 (s), 33.3 (q), 36.8 (s), 39.2 (t), 40.7 (t), 41.7 (t), 52.5 (d), 56.0 (d), 60.61 (t), 62.33 (t), 64.73 (t), 77.0 (s), 106.0 (s), 119.8 (d), 133.2 (s), 139.7 (d), 148.0 (s), 156.2 (s)
5. Solubility: hardly soluble in water, soluble in hydrated solvent such as an aqueous solution of 10% to 100% methanol or an aqueous solution of 10% to 100% acetonitrile, and soluble in less-polar organic solvents such as hexane or chloroform.

Figure 12:
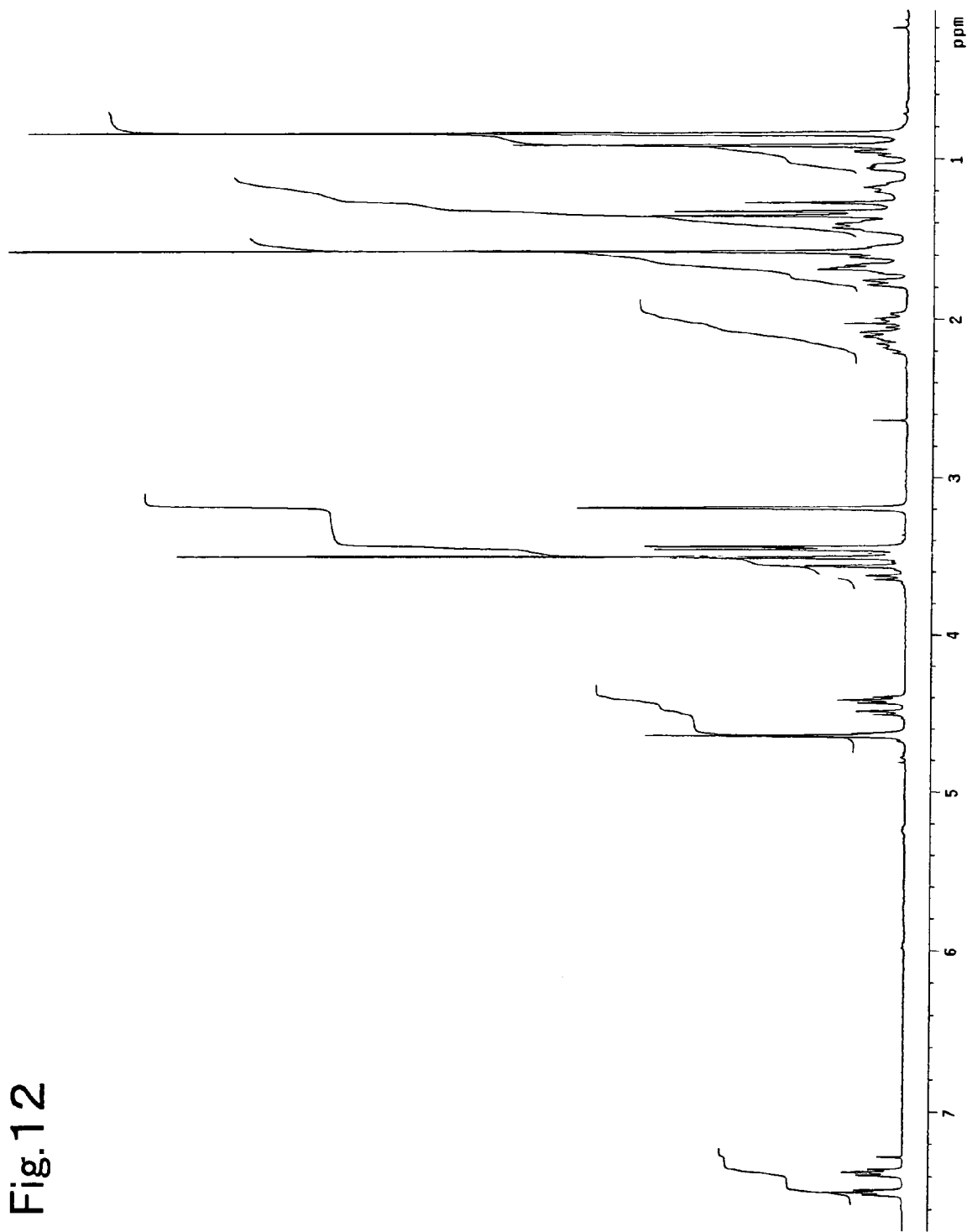
FIG. 12 shows a $^1$H-NMR spectrum of Me1H1Me.

[Physicochemical Properties of Me1H1Me]
1. Color of substance: colorless
2. Molecular weight: 457
3. Mass spectrometry: FABMS: m/z 458 [M+H]$^+$
4. Nuclear magnetic resonance signal:
1) $^1$H-NMR (deuterium chloroform, 500 MHz): (FIG. 12)
δ ppm 0.847 (6H, s), 0.921 (3H, s), 0.96 (1H, m), 1.05 (1H, m), 1.18 (1H, m), 1.331 (3H, s), 1.36 (1H, m), 1.41 (1H, m), 1.43 (1H, m), 1.57 (1H, m), 1.59 (1H, m), 1.67 (1H, m), 1.68 (1H, m), 1.77 (1H, br d, J=13 Hz), 2.00 (1H, m), 2.09 (1H, m), 2.16 (1H, m), 3.19 (3H, br s), 3.45 (3H, br s), 3.509 (3H, s), 3.564 (2H, d, J=12 Hz), 4.419 (2H, dd, J=8.5, 10.5 Hz), 4.644 (2H, br s), 7.356 (1H, d, J=7.0 Hz), 7.488 (1H, d, J=7.0 Hz)
2) $^{13}$C-NMR (deuterium chloroform, determination of chemical shift based on HMBC (Heteronuclear Multiple Bond Coherence) and HSQC (Heteronuclear Single Quantum Coherence) spectrum)
δ ppm 15.0 (q), 18.7 (t), 20.0 (t), 20.6 (q), 21.7 (q), 26.2 (t), 33.2 (s), 33.5 (q), 36.9 (s), 39.4 (t), 41.0 (t), 42.0 (t), 52.8 (d), 56.2 (d), 58.4 (q), 59.0 (q), 59.1 (q), 70.2 (s), 74.0 (s), 75.6 (s), 76.9 (s), 109.9 (s), 120.5 (d), 135.1(s), 139.2 (d), 145.7 (s), 155.1 (s)
5. Solubility: hardly soluble in water, soluble in hydrated solvent such as an aqueous solution of 30% to 100% methanol or an aqueous solution of 30% to 100% acetonitrile, and soluble in less-polar organic solvents such as hexane or chloroform.

Example 5

Minimum Effective Concentration (MEC) of the Novel Chemical Substance 1

Similar to the case of Example 1, isolated and purified novel chemical substance 1 was serially diluted in 16 steps starting with the final concentration of 1 μg/ml. At this time, the *Monostroma oxyspermum* cell number was adjusted to be 20 cells per 1 ml of the medium. Fresh pipet tips were used for each step dilution. Three sets of these series were prepared and were cultivated for 3 days under the same condition as Example 1. As a result, the thallus formation of *Monostroma oxyspermum* was observed at the set of 12-step dilution. Based on this, the MEC of the novel chemical substance 1 will be as follows.

1 μg/ml×10$^{-12}$=1 ag/ml (atto-gram per milliliter)

Figure 13:
FIG. 13 is a picture of Example 5 of 7 step serial dilution after culturing for 10 days.
Figure 14:
FIG. 14 is a picture of Example 5 of 6 step serial dilution after culturing for 10 days.

As the cultivating period becomes longer, the novel chemical substance 1 is used up by the *Monostroma* grown in the medium, and the thallus will be collapsed. FIG. 13 shows a picture of a seven-step dilution (final concentration of the novel chemical substance 1: 1×10$^{-7}$ μg/ml) cultivated for 10 days. Although traces of thallus are recognized, the disrupted thallus is observed. FIG. 14 shows a picture of a six-step dilution (final concentration of the novel chemical substance 1: 1×10$^{-6}$ μg/ml) cultivated for 10 days. The thallus was maintained without being collapsed, and MEC after 10 days cultivation was as follows.

1 μg/ml×10⁻⁶=1 pg/ml (pico-gram per milliliter).

Under the conditions specified in Example 1, *Monostroma oxyspermum* cells divide approximately twice a day. Therefore, if the initial number of the cells is 20, the cell number will be calculated to be 20×(2×2)³=1,280 cells after 3 days, and it will be 20×(2×2)¹⁰=20,971,520 cells after 10 days. Compared to the number at day 3, the cell number increases 10,000 fold after 10 days, indicating that this is how MEC values change largely depending on the cell number and cultivating length. In short, the novel chemical substance 1 needs to be supplemented in accordance with the cultivating length and cell growth appropriately.

Example 6

Activities of the Novel Chemical Substance 1 and its Derivatives

Similar to Example 5, the MEC of the novel chemical substance 1 and its derivatives are measured and the results are shown below.

TABLE 7

| MEC | |
|---|---|
| Novel Chemical Substance 1 | $10^{-12}$ μg/ml |
| Me1 | $10^{-4}$ μg/ml |
| Me1H3 | $10^{-2}$ μg/ml |
| Me1H1 | No activity |

The activity was reduced to $1/10^8$ when the novel chemical substance 1 was methylated. Based on this, as shown in Example 4, the functional groups to be methylated with methylating agents such as trimethylsilyldiazomethane were important for the activity.

Example 7

Culturing Experiment of *Ulva Pertusa* and *Enteromorpha Intestinalis*

Figure 15:
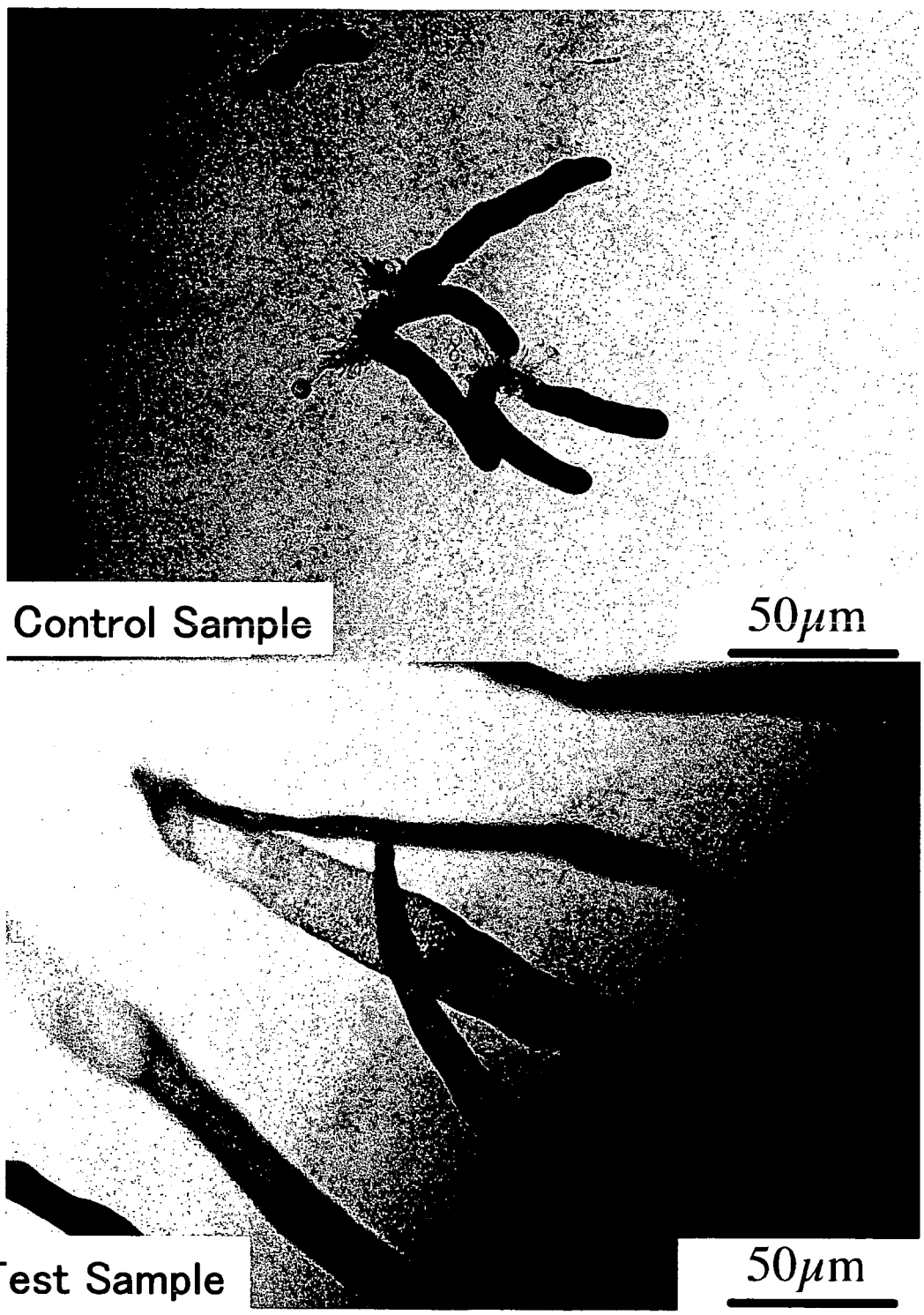
FIG. 15 is a picture of *Ulva pertusa* in accordance with Example 7.
Figure 16:
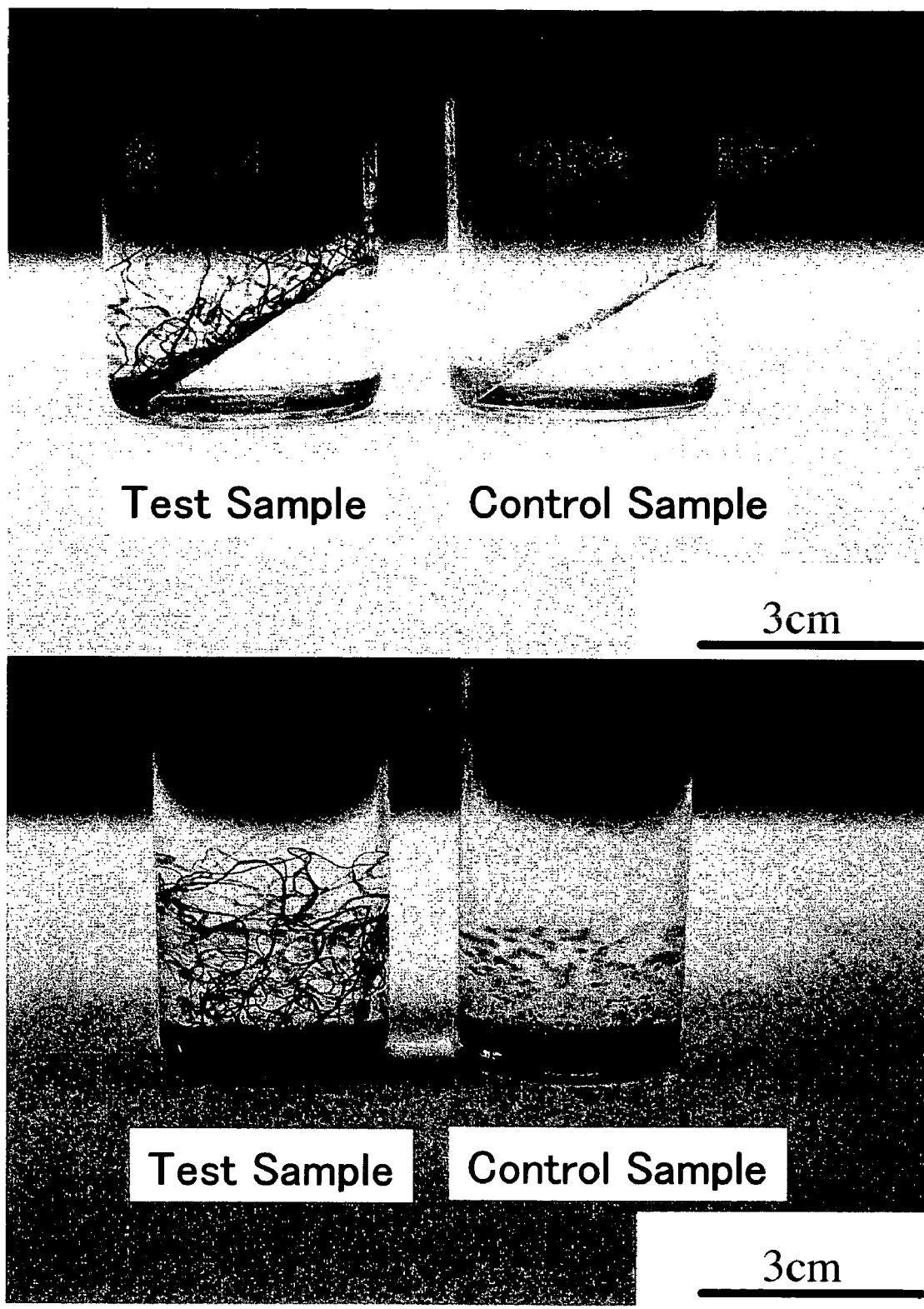
FIG. 16 is a picture of *Enteromorpha interstinalis* in accordance with Example 7.

Spores obtained from the *Ulva pertusa* and *Enteromorpha intestinalis* collected from Miho Shimizu-city, Shizuoka were washed using their phototaxis activity in the ASP7 medium supplemented with the antibiotics, and then were transferred to rectangular petri dishes filled with sterilized covered glasses and aseptized for 5 days. When the free-living cells had attached to the cover glasses and had start growing, each cover glass was placed in each hole of 6-MTP, followed by adding 10 ml of the ASP7 medium not supplemented with antibiotics. For a test group, the novel chemical substance 1 was added to result in 1 ng/ml and for the control group, nothing was added. They were incubtaed for 7 days under the same conditions as in Example 1. On day 10, the cover glasses of the test group and control section were transferred to the culture test tube containing the medium prepared under the same condition to further incubate another 7 days. FIG. 15 and 16 shows the test results of *Ulva pertusa* and *Enteromorpha intestinalis*, respectively. As seen clearly by comparing the test and control groups, rhizoids of the green alga were abnormally developed and the regular thallus formation was not observed in the control group, but normal development and thallus formation were observed when the novel chemical substance 1 was added. In addition, the ASP7 medium supplemented with antibiotics is an ASP medium, having the following composition and containing 2% antibiotics.

TABLE 8

| Antibiotic Mixture | |
|---|---|
| Distilled Water | 1000 ml |
| Penicillin | 100 mg |
| Streptomycin | 200 mg |
| Kanamycin | 100 mg |

Example 8

Specific Activity of Morphogenesis-Inducing Activity Against Foliate Green Alga

Figure 17:
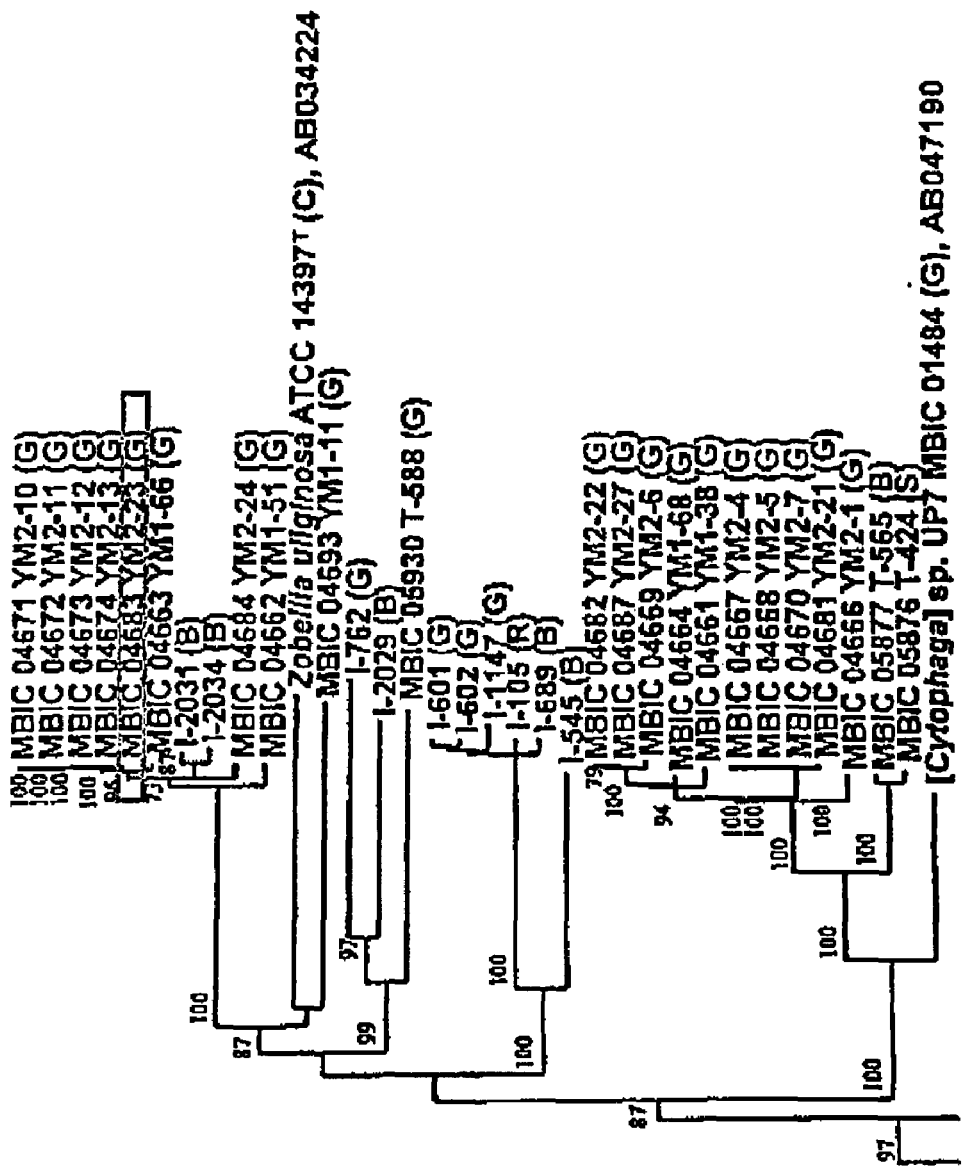
FIG. 17 is a phylogenetic tree based on the nucleotide sequences of gyr B DNA of YM-1-69 strain, YM-2-23 strain and their analogous strains.
Figure 17:
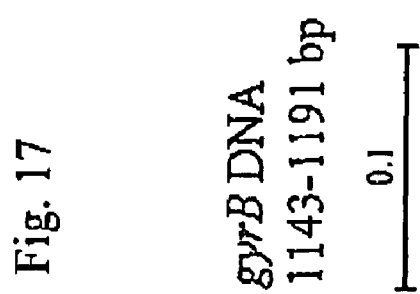
Figure 17:
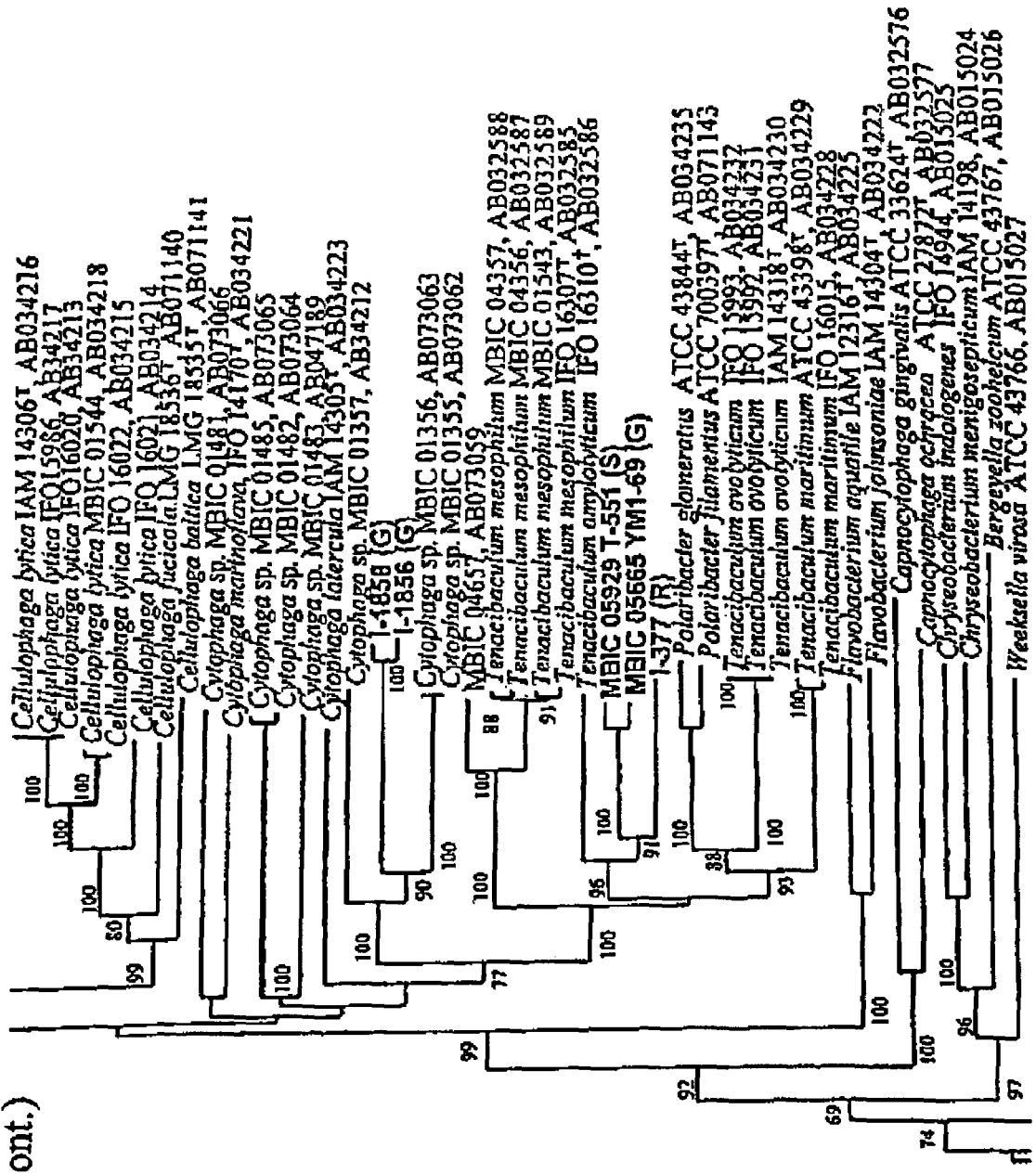
Figure 17:
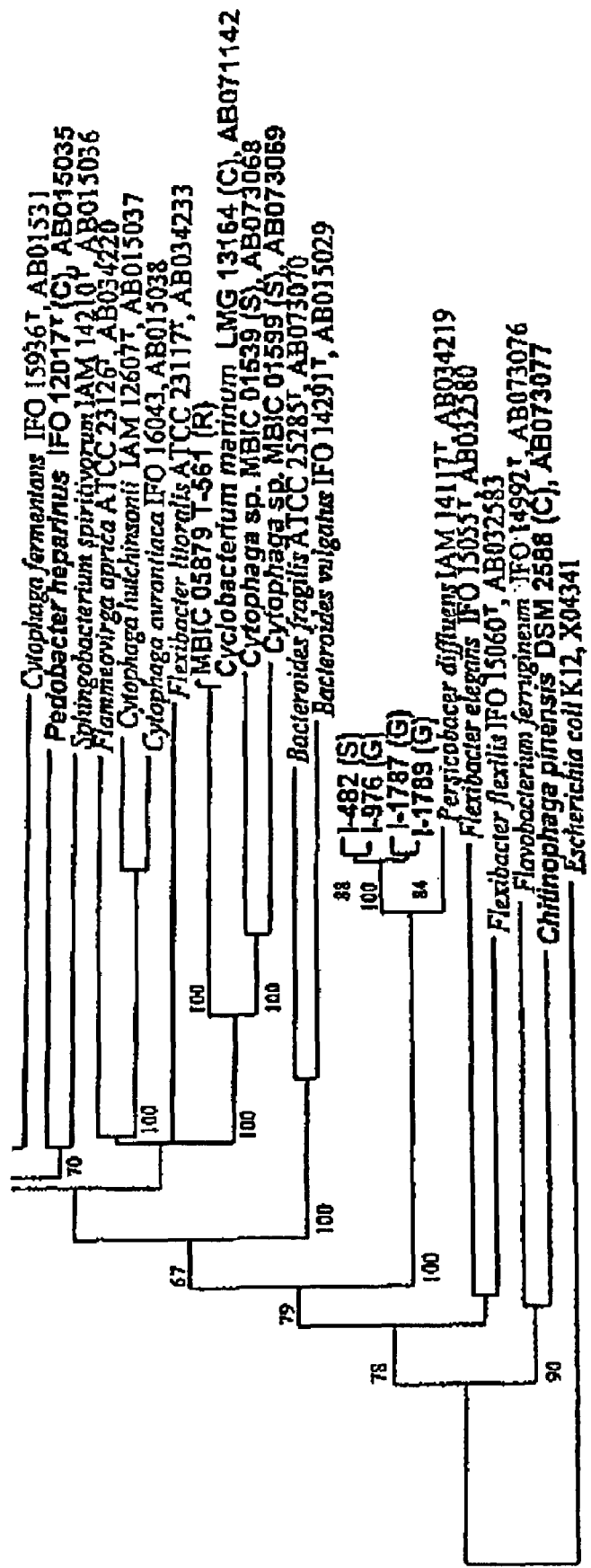
Figure 18:
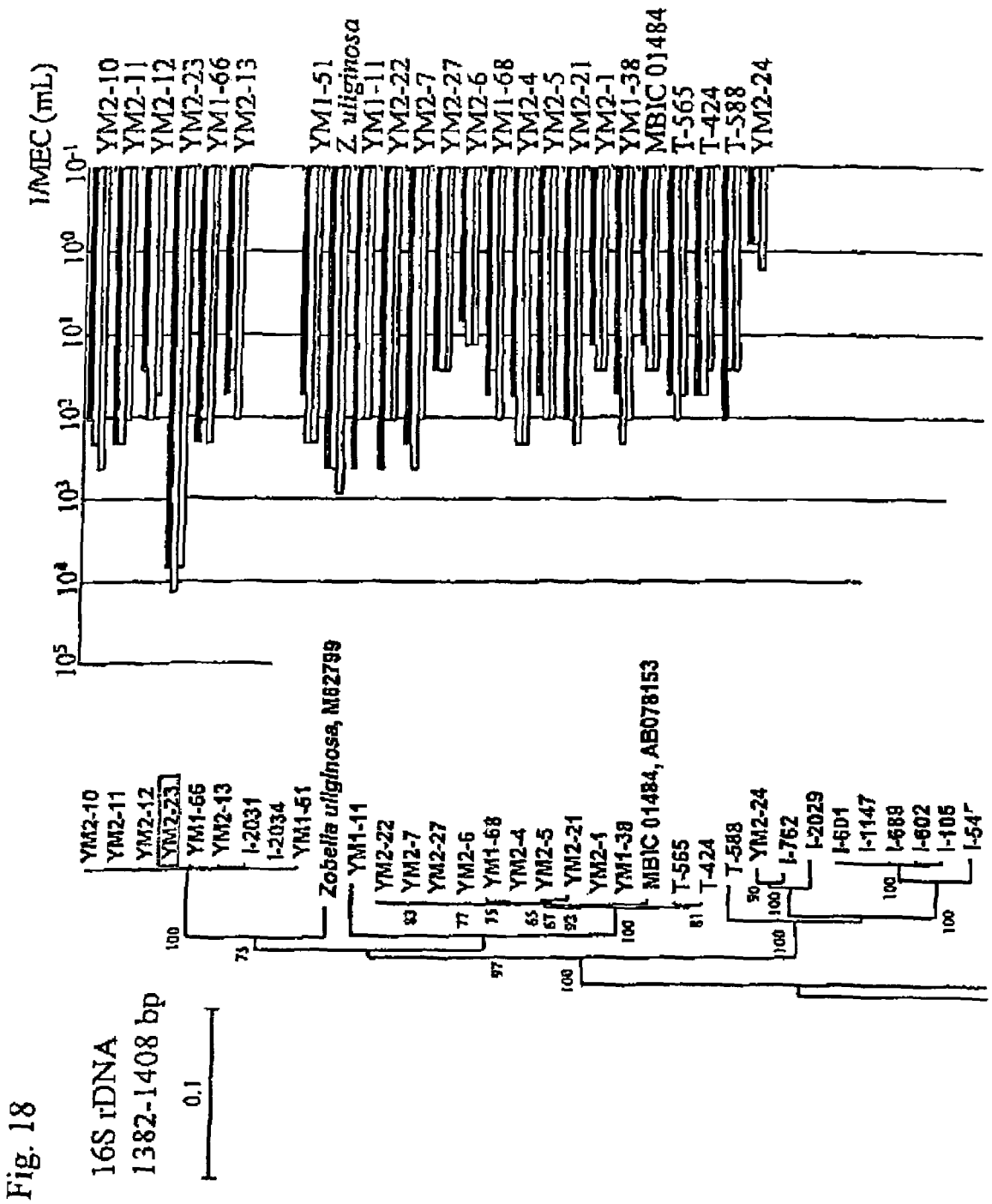
FIG. 18 is a phylogenetic tree based on the nucleotide sequences of 16Sr DNA of YM-1-69 strain, YM-2-23 strain and their analogous strains, and specific activities of morphogenetic induction against foliate green alga of these strains.
Figure 18:
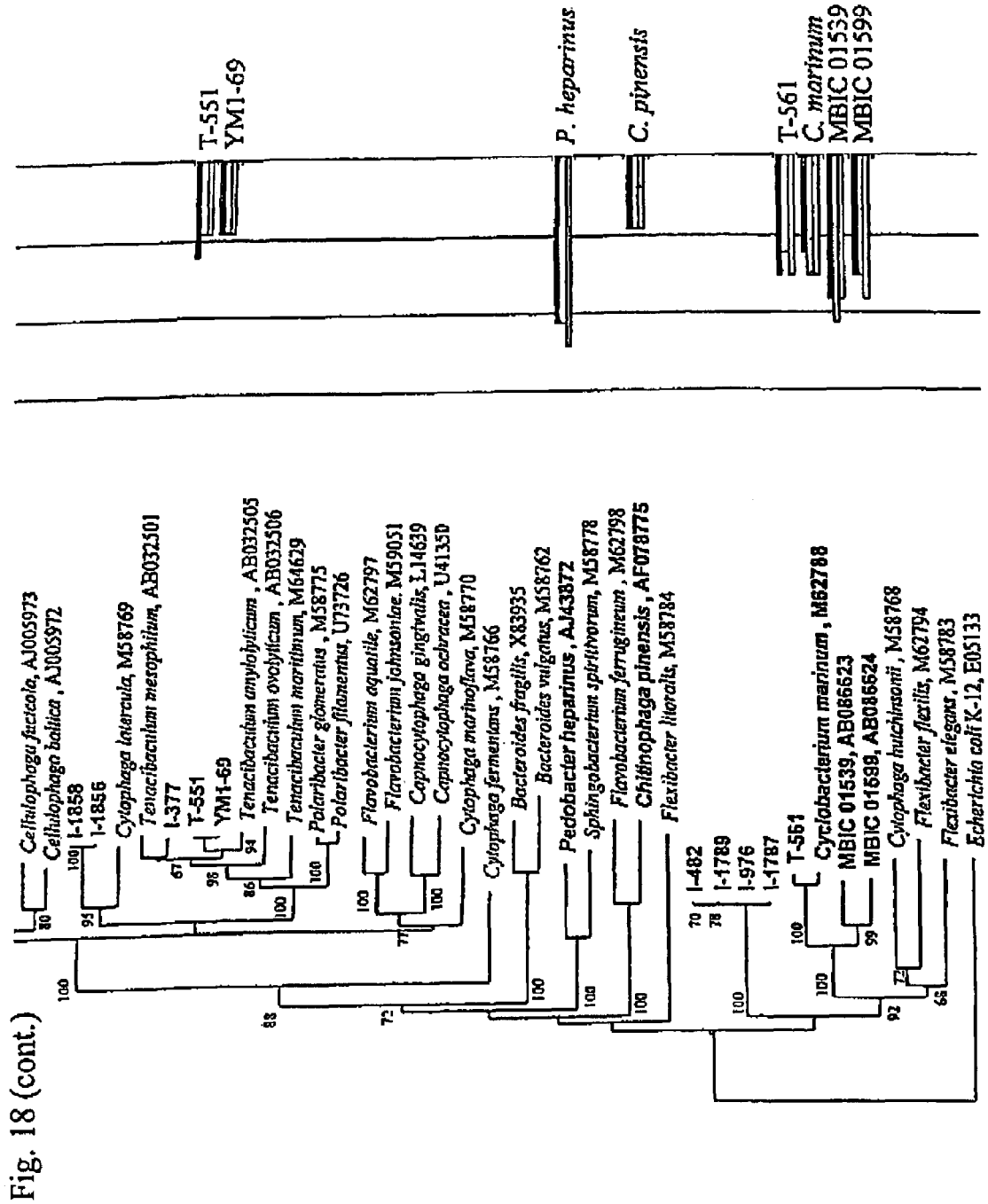

Similar to Example 5, the MEC were determined for the YM-1-69 strain, the YM-2-23 strain, and the analogous strains shown in FIG. 17 and shown in FIG. 18 In this figure, the Y-axis indicates the amount of *Monostroma oxyspermum* (ml) can be activated by the addition of 1 μl of the supernatant of the culture media. For instance, YM-2-23 strain is capable of activating approximately 8000 ml of *Monostroma oxyspermum* with 1 μl of the supernatant of the culture media in accordance with FIG. 18.

Example 9

Preparation and Physiochemical Properties of Me1H1W4 Cyclized Form

A 6.8 mg sample of Me1H1 obtained from Example 1 was dissolved in 10 ml of methanol, then was stirred for approximately 1 hour at room temperature after adding 0.5 ml of 6 M hydrochloric acid 0.5 ml. The solution was dried under reduced pressure with an evaporator, and was separated, followed by separation by high-performance liquid chromatography (TSKgel ODS-80 Ts, 4.6 mm (inner diameter)×150 mm (length), Tosoh) using 50% to 100% acetonitrile-water as a mobile phase. As a result, a cyclized form of Me1H1 (hereafter abbreviated as "Me1H1W4" was obtained at high yield (Yield approximately 5 mg, 74%). Moreover, the similar results were obtained by allowing the above reactions with hydrated methanol at room temperature for a long time.

[Physiochemical Properties of Me1H1W4]

1. Color of Substance: Colorless
2. Melting Point: 215.5-216.5° C. (Re-crystallization Solvent: Diethyl ether-acetone)
3. Molecular Weight: 415
4. Molecular Formula: $C_{25}H_{37}NO_4$ Mass Spectroscopy: CIMS: m/z b 416 [M+H]⁺

High Resolution Mass Spectroscopy: Actual Value: 416.2781; Calculated Value: 416.2774

Figure 19:
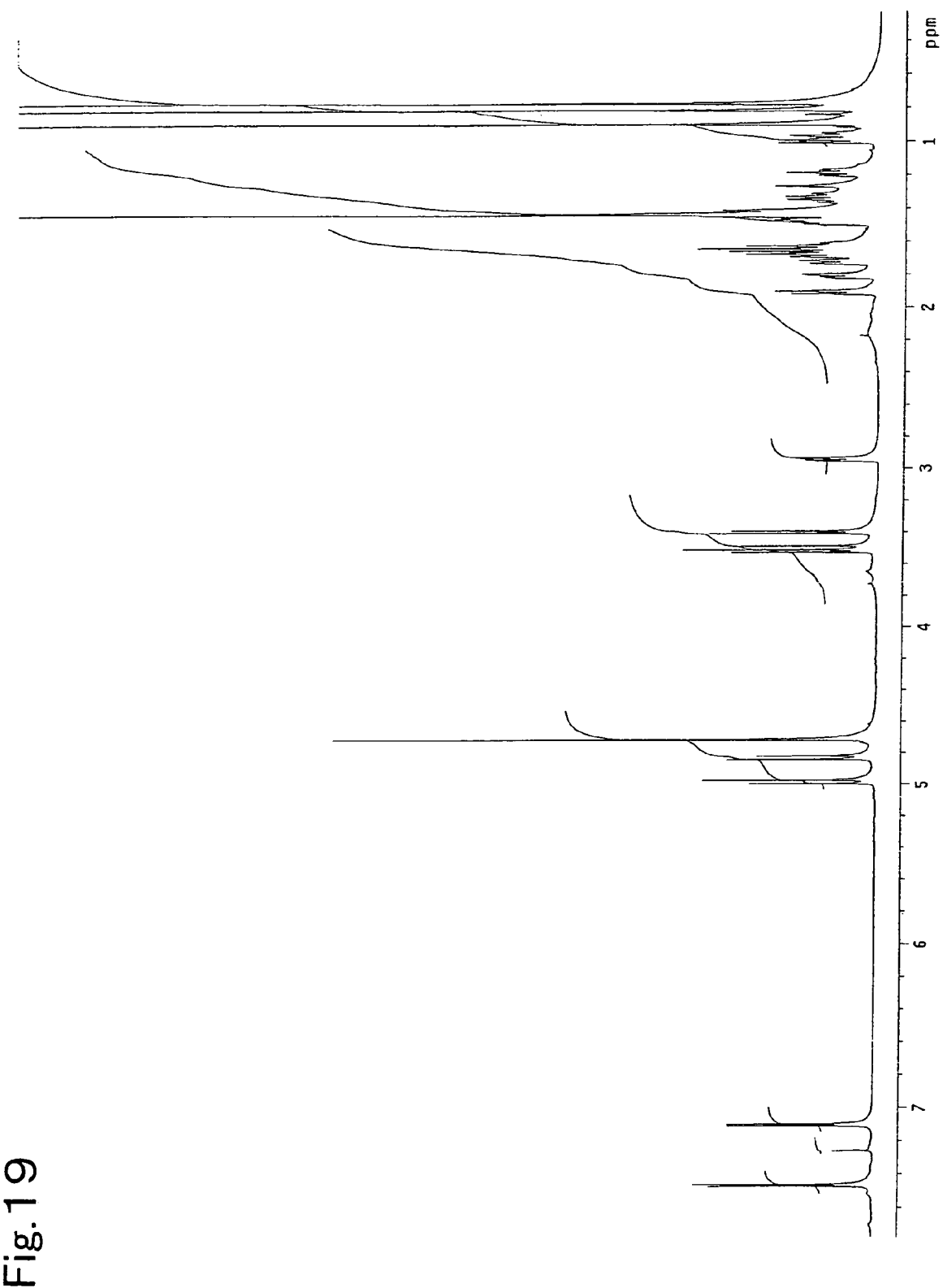
FIG. 19 shows a $^1$H-NMR spectrum of Me1H1W4.

5. Nuclear Magnetic resonance signal:

1)¹H NMR (Chloroform-d1, 750 MHz): (FIG. 19)

δ ppm 0.776 (3H, s), 0.816 (3H, s), 0.899 (3H, s), 0.996 (1H, ddd, J=3, 13, 13 Hz), 0.999 (1H, dd, J=2, 12 Hz), 1.186 (1H, ddd, J=3.8, 13, 14 Hz), 1.330 (1H, ddd, J=3, 13, 14 Hz), 1.40 (1H, m), 1.42 (1H, m), 1.439 (3H, s), 1.45 (1H, m), 1.46 (1H, m), 1.62 (1H, m), 1.64 (1H, m), 1.66 (1H, m), 1.726 (1H, m), 1.810 (1H, ddd, J=2, 5, 14 Hz), 1.911 (1H, ddd, J=3, 4, 13 Hz), 2.958 (1H, dd, J=5.1, 12 Hz), 3.361 (1H, d, J=12 Hz), 3.422 (1H, d, J=12 Hz), 4.627 (2H, br s), 4.801 (1H, d, J=17 Hz), 4.899 (1H, d, J=17 Hz), 7.393 (1H, d, J=7.8 Hz), 7.654 (1H, d, J=7.8 Hz)

Figure 20:
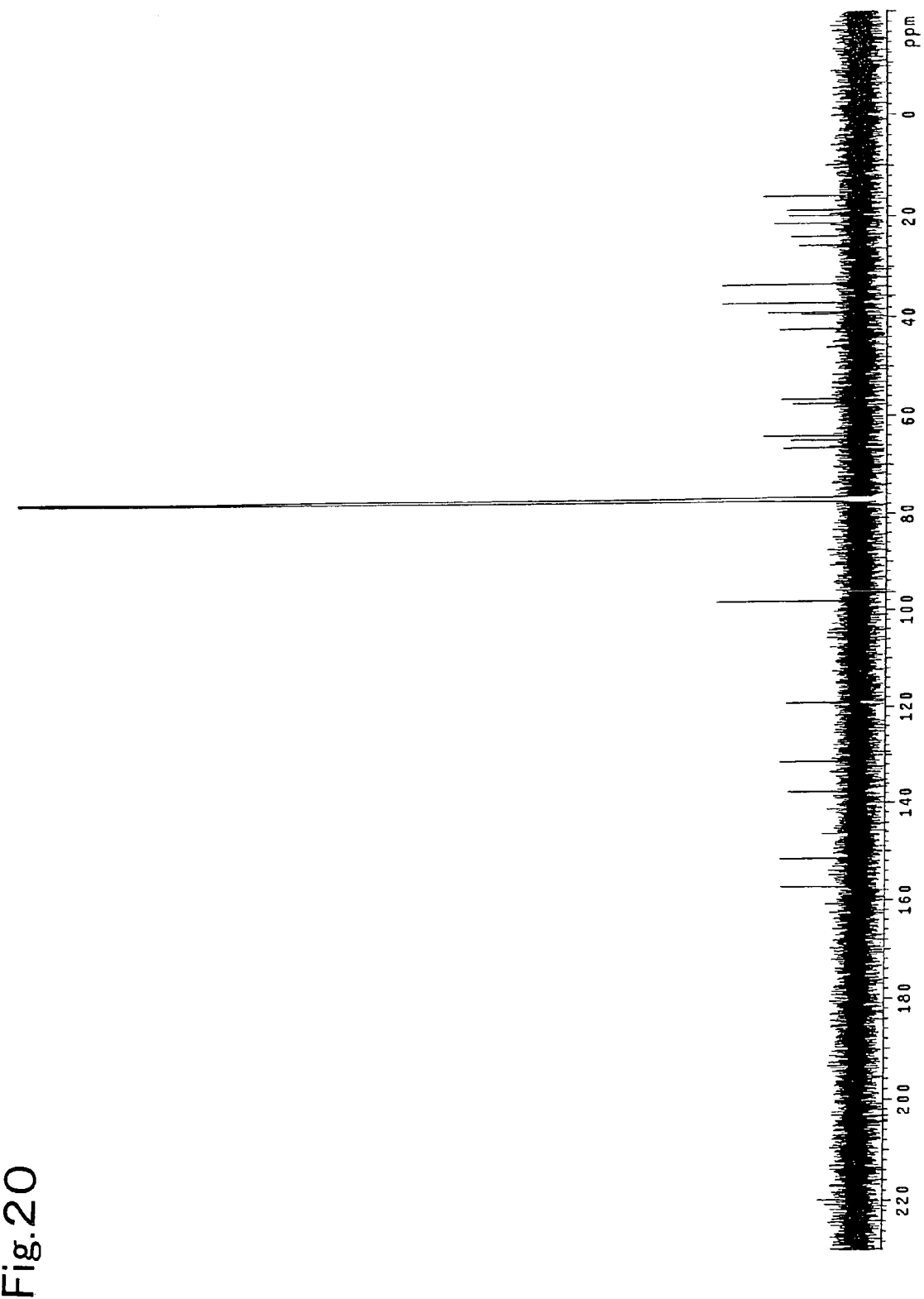
FIG. 20 shows a $^{13}$C-NMR spectrum of Me1H1W4.

2) $^{13}$C-NMR (Chloroform-d1, 187.5 MHz): (FIG. 20)

δ ppm 15.8 (q), 18.5 (t), 19.7 (t), 21.2 (q), 23.9 (q), 25.6 (t), 33.3 (s), 33.3 (q), 37.0 (s), 39.2 (t), 38.9 (d), 42.1 (t), 42.3 (t), 56.5 (d), 57.4 (d), 63.9 (t), 64.8 (t), 66.4 (t), 77.4 (s), 98.1 (s), 119.0 (d), 131.3 (s), 137.6 (d), 151.4 (s), 157.2 (s)

6. Solubility: Poorly soluble in water, soluble in hydrated solvents such as 50% to 100% methanol solution or 50 to 100% acetonitrile solution and less-polar organic solvents such as chloroform and toluene, and hardly soluble in non-polar solvent such as hexane.

Example 10

X-ray Crystallographic Analysis of the Me1H1W4 Cyclized Form

Figure 21:
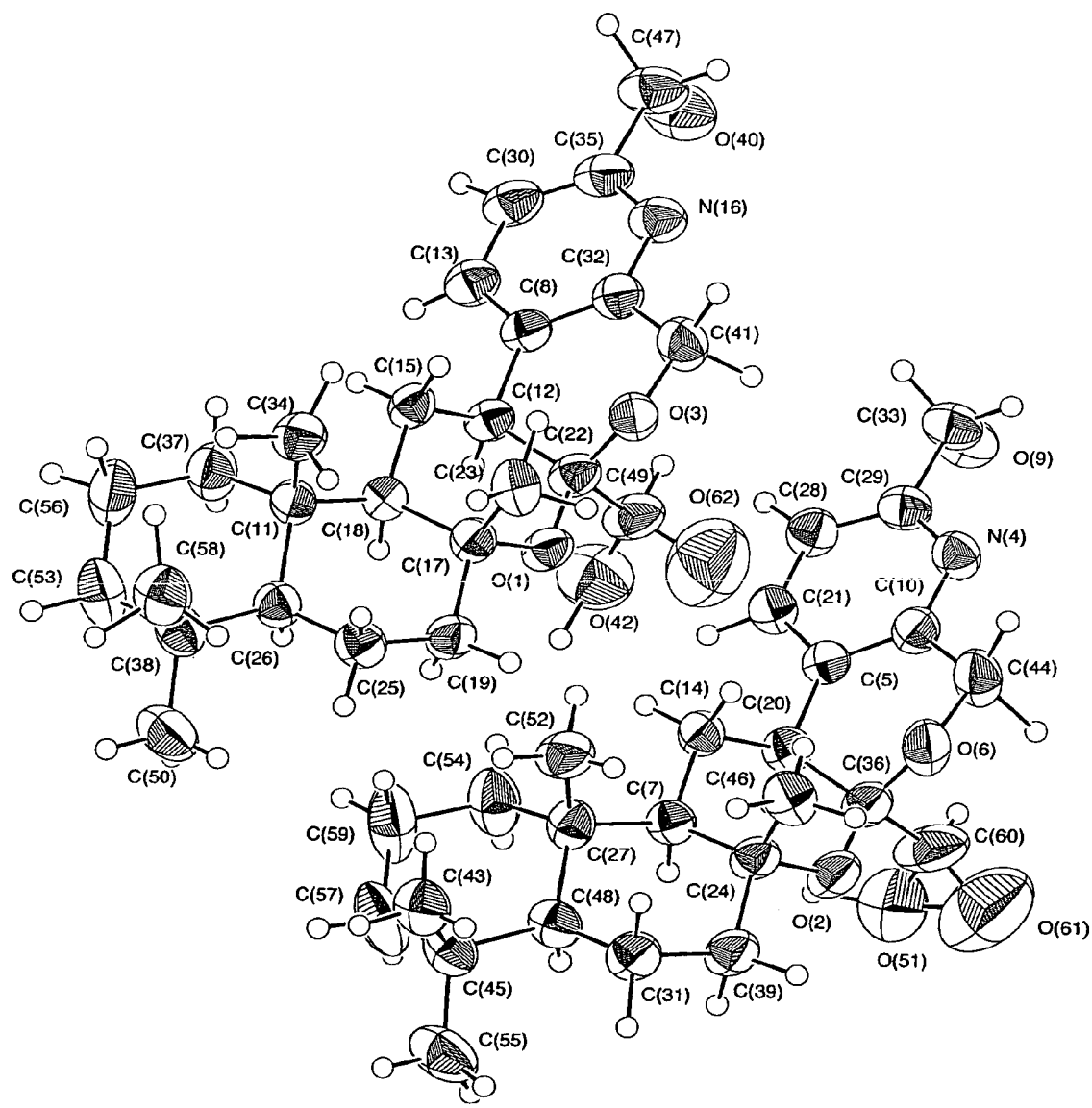
FIG. 21 shows an X-ray crystallographic analysis of Me1H1W4.

Purified Me1H1W4 cyclized form can be easily crystallized in an appropriate solvent system, monoclinic single crystal was obtained when it was re-crystallized with diethyl ether-acetone. the crystal was analyzed with X-ray crystallography, and its ortep drawing is shown in FIG. 21. Moreover, Table 9 shows the data of the crystal. Based on this ortep diagram, the structure of Me1H1W4 is as in Formula 1:

Formula 1:

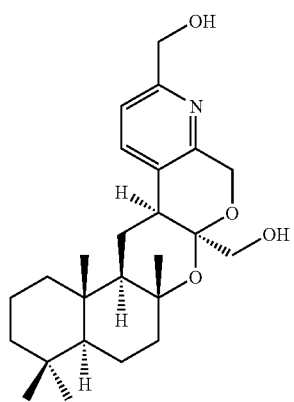

In addition, as shown in Example 9, its precursor Me1H1 and Me1 described in Example 4 are shown in Formula 2:

Formula 2:

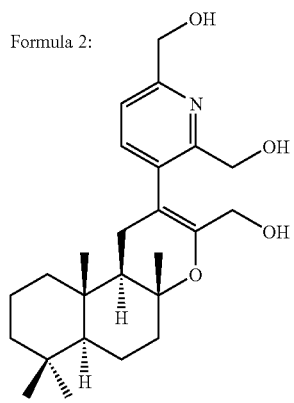

and Formula 3:

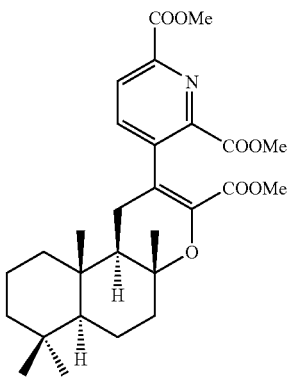

, respectively. The structural formula for the novel chemical substance 1 is shown in Formula 4:

TABLE 4

| Crystal data | |
|---|---|
|  |  |
|  | V = 4585.6 (4) Å$^3$ |
| $C_{25}H_{37}NO_4$ | Z = 8 |
| $C_{25}H_{37}NO_4$ | $D_x$ = 1.204 Mg m$^{-3}$ |
| $M_r$ = 415.574 | Density measured by: not measured |
| Monoclinic | fine-focus sealed tube |
| C2 | Mo Kα radiation |
| a = 33.103 (2) Å | λ = 0.71073 |
| b = 9.1120 (4) Å | μ = 0.080 mm-1 |
| c = 15.3240 (10) Å | T = 298 K |
| α = 90.00° | Cube |
| β = 97.217 (2)° | Colourless |
| γ = 90.00° | Crystal source: Local laboratory |
| Data collection | |
|  |  |
|  | Criterion: >2sigma(I) |
| DIP Image plate | θ$_{max}$ = 25.72° |
| Absorption correction: sphere | h = −39→39 |
| T$_{min}$ = 0.959, T$_{max}$ = 0.959 | k = −10→10 |
| 7315 measured reflections | l = −18→18 |
| 7315 independent reflections | |
| 6796 observed reflections | |
| Refinement | |
|  |  |
|  | Only coordinates of H atoms refined |
| Refinement on F$^2$ | Calculated weight calc |
| full matrix lease | Δ/σmax = 0.066 |
| squares | Δρmax = 0.254 eÅ$^3$ |
| refinement | Δρmin = −0.560 eÅ$^3$ |
| R(all) = 0.0734 | Extinction correction: none |
| R(gt) = 0.0696 | Atomic scattering factors from |
| wR(ref) = 0.2123 | International Tables Vol C |
| wR(gt) = 0.2064 | Tables 4.2.6.8 and 6.1.1.4 |
| S(ref) = 1.073 | Flack parameter = 1.9 (15) |
| 7315 reflections | Flack H D (1983), Acta Cryst. A39, |
| 559 parameters | 876-881 |
| 1 restraints | |
| Data collection: DIP Image plate | |
| Data reduction: maXus (Mackay et al., 1999) | |
| Program(s) used to refine structure: SHELXL-97 (Sheldrick, 1997) | |

Formula 4:

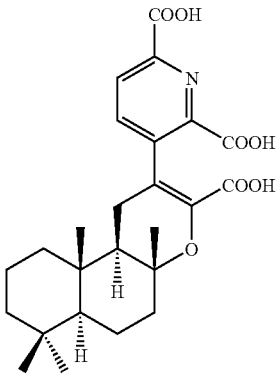

All the publications, patents and patent applications cited in this application are incorporated herein by reference in their entirety.

INDUSTRIAL APPLICABILITY

The present invention is to provide novel culturing and cultivating techniques of marine foliate green alga such as *Ulva lactuca* and *Monostroma nitidum* using the novel chemical substances. In accordance with the present method, this invention allows aseptic culture in experimental laboratories. The spores are easily maintained and managed, furthermore, the marine foliate alga is safely grown and produced in the cultivation farm.

SEQUENCE LISTING

A sequence listing in paper format and in computer-readable format accompanies this application.

SEQUENCE LISTING

```
<160> NUMBER OF SEQ ID NOS: 4

<210> SEQ ID NO 1
<211> LENGTH: 190
<212> TYPE: DNA
<213> ORGANISM: Tenacibaculum sp.

<400> SEQUENCE: 1
cctacgggag gcagcagtga ggaatattgg tcaatggagg caactctgaa ccagccatgc      60
cgcgtgtagg aagactgccc tatgggttgt aaactacttt tatatgggaa gaaaccctc    120 ttacgtgtag aggcttgacg gtaccataag aataagcacc ggctaactcc gtgccagcag   180
ccgcggtaat                                                           190

<210> SEQ ID NO 2
<211> LENGTH: 189
<212> TYPE: DNA
<213> ORGANISM: Unknown
<220> FEATURE:
<223> OTHER INFORMATION: DNA nucleotide sequence of V3 region in 16S
      rRNA of YM-2-23 strain being identified as
      Cytophaga-Flavobacterium-Bacteriodes complex

<400> SEQUENCE: 2
cctacgggag gcagcagtga ggaatattgg acaatgggcg ggagcctgat ccagccatgc     60
cgcgtgcggg aagaaggccc tatgggtcgt aaaccgcttt tatacgggaa gaaaccaccc   120
tacgtgtagg gtactgacgg taccgtaaga ataaggaccg gctaactccg tgccagcagc   180
cgcggtaat                                                            189

<210> SEQ ID NO 3
<211> LENGTH: 1173
<212> TYPE: DNA
<213> ORGANISM: Tenacibaculum sp.

<400> SEQUENCE: 3
gtatctggag gtttacacgg agttggtgta tcttgtgtga atgcactttc agatcattta     60
aaagctacag ttcacagaga aggtaaaata tgggaacaag agtatgaacg tggtaaaaca   120
ctttatcctg taaaaactgt aggtgaaact gatataactg gtacagaagt aactttctta   180
```

```
ccagacaaaa gtattttcca acaaaccaca gaatataatt acgaaacgtt agctacacgt      240
atgcgtgagt tagcgtatct taataaagga atcacgatta cgttaacaga taagcgtaat      300
aaagatgatg aaggaaattt tattgctgaa actttccaca gtaacgaagg attatctgaa      360
tttgttaaat atttagatag tactcgtact cctgttattc agcatgtaat ttcaatggaa      420
ggtgagaaaa acgaattcc tgttgaggtt gcaatgattt ataatgattc atatgctgaa      480
aatttacatt cttatgtaaa taacattaat actcacgaag gaggaacaca tttatcagga      540
tttagaagag gttaacaag tactttaaag aaatatgcag atacttctgg attactaaag      600
aacgttaagt ttgagatttc tggagatgat ttccgtgaag gtttaacggc aattgtatct      660
gtaaaagtag ctgaacctca gtttgaagga caaacaaaaa caaaattagg aaacagagaa      720
gttacttctg cagtatcgca agctgtagca gaaatgttaa ctgattattt agaggaaaat      780
cctaatgatg ctaaaacgat tgtacaaaaa gtaattcttg cagctcaagc gcgtcacgca      840
gctcgtaaag caagagaaat ggtgcaacgt aaaacagtaa tgagtattgg aggtttacct      900
ggtaaactat ctgattgttc tgaaactgat ccagcagttt gtgaatttt cttagtcgag      960 ggagattcgg caggtggaac tgcaaaacaa ggtcgtgatc gtaatttcca agcaattta     1020 cccttacgtg gtaagattct taacgtagaa aaagcgatgc agcataaagt ttttgagaat     1080
gaagaaatca aaaacatgtt tacggcttta ggaatcacta tcggaacaga agaagatcca     1140
agagcattaa acttatcaaa attaagatat cat                                  1173

<210> SEQ ID NO 4
<211> LENGTH: 1173
<212> TYPE: DNA
<213> ORGANISM: Unknown
<220> FEATURE:
<223> OTHER INFORMATION: DNA nucleotide sequence of gyrB gene of YM-2-23
      strain being identified as
      Cytophaga-Flavobacterium-Bacteriodes c

<400> SEQUENCE: 4
gtatccggtg gtttgcacgg ggtaggtgtt tcttgtgtga acgccctttc caatcatctt       60
aaagctaccg tacatagaga tgggaaagtt tgggaacagg aatatgaacg gggtaaatcc      120
ctttatcccg taaaagtgt tggggagacc gatgaaactg gaaccattgt taccttcata      180
ccagatgatt caatctttac ccaaacaaca gagtatagtt atgagaccct tgccaacaga      240
atgcgtgagc tttcgttctt gaacaaaggg gttaccatta gcattacgga caaaagagta      300
aaggataaag aaggggagta ccttttctgaa acttttttatt ccgatgctgg actaagtgaa      360
tttgttaagt tcttggatgg tacccgtgaa cctttgattc aagggggttat cgcgatggaa      420 ggggagaaaa atggtatccc tgtggaagtg gcaatggttt acaacaccag ttacacggag      480
aatttacatt cctatgtgaa taacattaac acgcacgaag ggggtacgca tctttccggt      540
tttagaaggg gattgacctc tactttaaag aaatacgcag attcttctgg aatgctcgag      600
aaattgaagt ttgaggttca gggagatgat ttccgtgaag gacttacagc aattgttttcc      660 gttaaggtcg cagaacctca atttgaaggt cagacgaaaa ccaagcttgg aaaccgcgag      720
gtttcttctg cggtgagcca agctgtttct gaaatgctca cggattattt ggaggagcat      780
ccagatgatg ccaaggttat tgttcaaaaa gttatccttg ccgctcaggc cagacatgcc      840
gctacaaagg cccgtgaaat ggtacagcgt aagacggtaa tgagtattgg tgggctacct      900
ggaaaattgt ccgattgttc tgagcaagat cctgcgcaat gtgaagtatt tcttgtagag      960
```

-continued

```
ggagattctg caggtggtac ggcaaaaatg ggccgggacc gaaaatttca ggccattctt    1020
ccactaaggg gtaaaatctt gaacgtggaa aaagccatgc agcacaaggt ttttgaaaat    1080
gaggaaataa agaatattta tacggcccta ggggttacta ttggaacgga agaagatagt    1140
aaggccttga acctggaaaa attaagatat cat                                 1173
```

Figure 2:
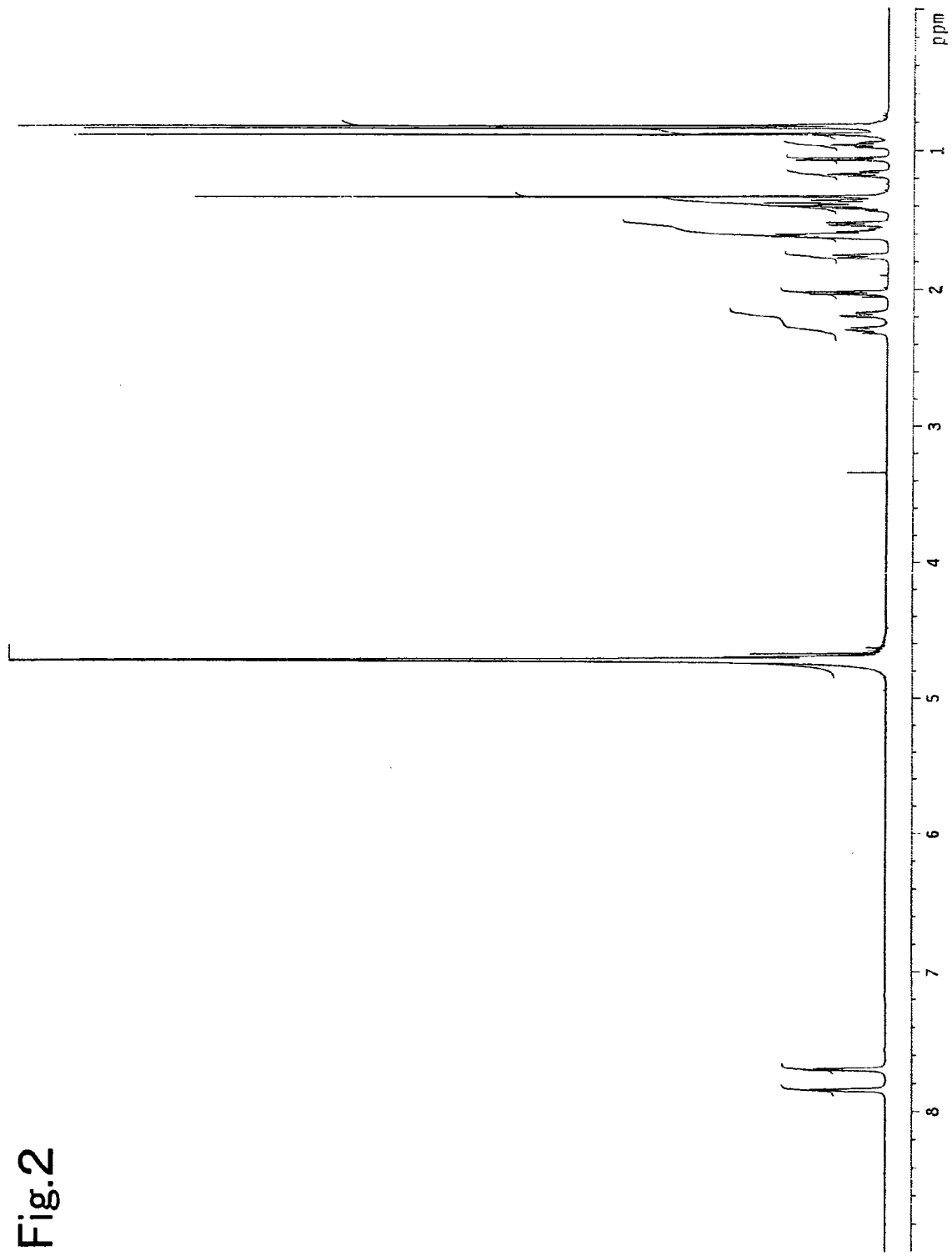
FIG. 2 shows a $^1$H-NMR spectrum of the novel chemical substance 1.
Figure 3:
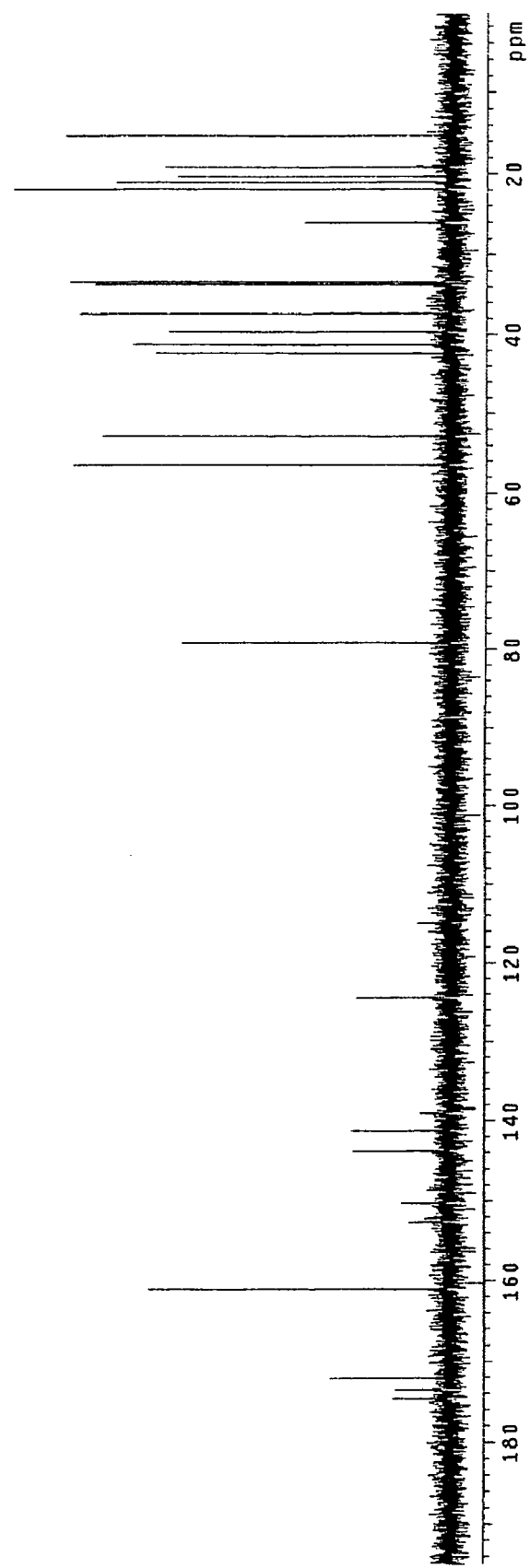
FIG. 3 shows a $^{13}$C-NMR spectrum of the novel chemical substance 1.

What is claimed is:

1. An isolated morphogenic and growth accelerating chemical substance 1 having the following physicochemical properties:

(i) color of substance: colorless;

(ii) molecular weight: 457;

(iii) mass spectrometry: FABMS:m/z 456 [M–H]⁻ (FIG. 1); and (iv) nuclear magnetic resonance signal:

1) $^1$H-NMR(D$_2$O-20 mM Na$_2$HPO$_4$ (pH 9), 750 MHz): (FIG. 2)

δ ppm 0.818 (3H, s), 0.837 (3H, s), 0.882 (3H, s), 0.960 (1H, m), 1.058 (1H, m), 1.167 (1H, m), 1.326 (3H, s), 1.37 (1H, m), 1.38 (1H, m), 1.40 (1H, m), 1.58 (1H, m), 1.61 (2H, m), 1.52 (1H, br d, J=13 Hz), 1.76 (1H, br d, J=14 Hz), 2.024 (1H, m), 2.181 (1H, dd, J=4, 14 Hz), 2.291 (1H, dd, J=14, 16.5 Hz), 7.698 (1H, d, J=7.5 Hz), 7.845(1H, d, J=7.5 Hz); and 2) $^{13}$C-NMR(D$_2$O-20 mM Na$_2$HPO$_4$ (pH 9), 125 MHz): (FIG. 3)

δ ppm 15.236 (q), 19.037 (t), 20.257 (t), 20.955 (q), 21.835 (q), 25.987 (t), 33.381 (s), 33.636 (q), 37.308 (s), 39.590 (t), 41.199 (t), 42.346 (t), 52.769 (d), 56.381 (d), 79.096 (s), 114.965 (s), 124.399 (d), 139.004 (s), 141.232 (d), 150.282 (s), 152.656 (s), 172.081 (s), 173.538 (s), 174.661 (s).

2. The chemical substance 1 according to claim 1, which is obtainable from the YM-2-23 strain (FERM BP-8417).

3. The chemical substance 1 according to claim 1, which is represented by the following formula:

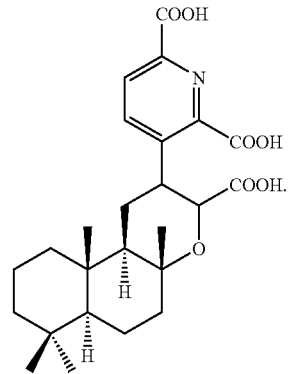

4. The chemical substance 1 according to claim 1, which has the molecular formula: C$_{25}$H$_{31}$NO$_7$.

5. A process for producing a chemical substance 1, wherein microorganisms capable of producing the chemical substance 1 according to claim 1 are cultured in medium, the chemical substance 1 is generated and accumulated in the cultures, and the generated and accumulated novel chemical substance 1 is recovered.

6. The production process according to claim 5, wherein the microorganisms are YM2-23 strain (FERM BP-8417), or an analogous strain thereof.

7. Culture medium for algae comprising, as an active ingredient, the chemical substance 1 according to claim 1.

8. A monomethylated, dimethylated, or trimethylated form of the chemical substance 1 obtained by treating the chemical substance 1 according to claim 1 with trimethylsilyldiazomethane.

9. A compound or a derivative thereof obtained by treating the trimethylated form according to claim 8 with sodium borohydride.

* * * * *